US012056890B2

United States Patent
Shin

(10) Patent No.: US 12,056,890 B2
(45) Date of Patent: Aug. 6, 2024

(54) METHOD FOR MEASURING VOLUME OF ORGAN BY USING ARTIFICIAL NEURAL NETWORK, AND APPARATUS THEREFOR

(71) Applicant: SYNERGY A.I. CO. LTD., Seongnam-si (KR)

(72) Inventor: Tae Young Shin, Chuncheon-si (KR)

(73) Assignee: Synergy A.I. Co. Ltd., Seongnam-si (KR)

( * ) Notice: Subject to any disclaimer, the term of this patent is extended or adjusted under 35 U.S.C. 154(b) by 527 days.

(21) Appl. No.: 17/312,342

(22) PCT Filed: Dec. 11, 2019

(86) PCT No.: PCT/KR2019/017514
§ 371 (c)(1),
(2) Date: Jun. 9, 2021

(87) PCT Pub. No.: WO2020/122606
PCT Pub. Date: Jun. 18, 2020

(65) Prior Publication Data
US 2022/0036575 A1     Feb. 3, 2022

(30) Foreign Application Priority Data

Dec. 11, 2018   (KR) ..................... 10-2018-0158812
Dec. 9, 2019    (KR) ..................... 10-2019-0162842

(51) Int. Cl.
*G16H 30/20*   (2018.01)
*G06T 7/62*    (2017.01)

(52) U.S. Cl.
CPC ............. *G06T 7/62* (2017.01); *G16H 30/20* (2018.01); *G06T 2207/10072* (2013.01);
(Continued)

(58) Field of Classification Search
None
See application file for complete search history.

(56) References Cited

U.S. PATENT DOCUMENTS

2011/0227914 A1* 9/2011 Varekamp ................. G06T 7/50
                                                         345/419
2018/0089840 A1*  3/2018 Yan ...................... G06T 7/0014
(Continued)

FOREIGN PATENT DOCUMENTS

JP      2002-230518 A     8/2002
JP      2015-205164 A    11/2015
(Continued)

OTHER PUBLICATIONS

International Search Report and Written Opinion mailed Mar. 18, 2020 in International Application PCT/KR2019/017514, in 8 pages. (English translation of ISR in 2 pages.).
(Continued)

*Primary Examiner* — Rinna Yi
(74) *Attorney, Agent, or Firm* — Knobbe, Martens, Olson & Bear, LLP

(57) ABSTRACT

This application relates to a method of measuring a volume of an organ. In one aspect, the method includes acquiring a plurality of captured images of the organ and photographing metadata and preprocessing the plurality of images to acquire a plurality of image patches of a specified size. The method may also include inputting the plurality of image patches into a three-dimensional (3D) convolutional neural network (CNN)-based neural network model and estimating an organ region corresponding to each of the plurality of image patches. The method may further include measuring a volume of the organ by using an area of the estimated organ region and the photographing metadata. The method may further include measuring an uncertainty value of the 3D CNN-based neural network model and uncertainty values of the plurality of images based on a result of estimating by the 3D CNN-based neural network model.

12 Claims, 15 Drawing Sheets

(52) U.S. Cl.
CPC .............. *G06T 2207/20081* (2013.01); *G06T 2207/20084* (2013.01); *G06T 2207/30056* (2013.01); *G06T 2207/30084* (2013.01)

(56) References Cited

U.S. PATENT DOCUMENTS

| | | | |
|---|---|---|---|
| 2018/0099152 | A1 | 4/2018 | Nioutsikou |
| 2018/0286037 | A1* | 10/2018 | Zaharchuk ................ G06T 5/50 |
| 2018/0330518 | A1 | 11/2018 | Choi |
| 2019/0090826 | A1* | 3/2019 | Carmi ..................... G06F 18/00 |
| 2019/0258932 | A1* | 8/2019 | Kang ....................... G06N 3/04 |
| 2020/0085382 | A1* | 3/2020 | Taerum ................. G06T 7/0016 |
| 2020/0175677 | A1* | 6/2020 | Mavroeidis .......... G06V 10/764 |
| 2020/0320354 | A1* | 10/2020 | Ghesu ................ G06F 18/2155 |

FOREIGN PATENT DOCUMENTS

| | | |
|---|---|---|
| JP | 2017-511239 A | 4/2017 |
| JP | 2017-202031 A | 11/2017 |
| KR | 10-0332072 B1 | 4/2002 |
| KR | 10-2015-0049585 A | 5/2015 |
| KR | 10-1659578 B1 | 9/2016 |
| KR | 10-1864412 B1 | 6/2018 |
| KR | 10-2019-0092299 A | 8/2019 |
| WO | WO 2015/157799 A1 | 10/2015 |
| WO | WO 2017/222970 A1 | 12/2017 |

OTHER PUBLICATIONS

Office Action of Korean Patent Application No. 10-2019-01692842—10 pages (Apr. 13, 2021).
Office Action of Korean Patent Application No. 10-2018-0158812—16 pages (Jun. 16, 2020).
Cardenas et al., "Auto-delineation of oropharyngeal clinical target volumes using 3D convolutional neural networks", Physics in Medicine & Biology, vol. 63—13 pages (Nov. 7, 2018).
Karimi et al., "Accurate and robust deep learning-based segmentation of the prostate clinical target volume in ultrasound images", Medical Image Analysis, vol. 57—11 pages (Jul. 15, 2019).
Kline et al., "Performance of an Artificial Multi-observer Deep Neural Network for Fully Automated Segmentation of Polycystic Kidneys", J Digit Imaging—7 pages (May 26, 2017).
Bae et al, "Novel Approach to Estimate Kidney and Cyst Volumes using Mid-Slice Magnetic Resonance Images in Polycystic Kidney Disease", American Journal of Nephrology, vol. 38, No. 4—9 pages (Oct. 5, 2013).
Aresta, et al., "iW-Net: an automatic and minimalistic interactive lung nodule segmentation deep network", arxiv.org, Cornell University Library, XP081042480, Nov. 30, 2018, in 7 pages.
Keshwani, et al., "Computation of Total Kidney Volume from CT Images in Autosomal Dominant Polycystic Kidney Disease Using Multi-task 3D Convolutional Neural Networks", Advances in Intelligent Data Analysis XIX:[Lecture Notes in Computer Science], pp. 380-388 XP04755884, ISBN: 978-3-540-354-3, Sep. 15, 2018, in 9 pages.
Lu, et al., "Automatic 3D liver location and segmentation via convolutional neural network and graph cut", International Journal of Computer Assisted Radiology and Surgery, Springer, DE, vol. 12, No. 2, Sep. 7, 2016, in 12 pages.
Sharma, et al., "Automatic Segmentation of Kidneys using Deep Learning for Total Kidney Volume Quantification in Autosomal Dominant Polycystic Kidney Disease", Scientific Reports, vol. 7 No.1, DOI: 10.1038/s41598*017-01779-0, May 17, 2017, in 10 pages.
Wang, et al., "Interactive Medical Image Segmentation using Deep Learning with Image-specific Fine-tuning", arxiv.org, Cornell University Library, Oct. 11, 2017, DOI: 10.1109/TMI.2018.2791721, in 11 pages.
Extended European Search Report in EP 19897034.5 dated Jan. 28, 2022 in 10 pages.
Japanese Notice of Allowance for JP 2021-533353 dated Jan. 31, 2023, in 5 pages.
Japanese Office Action for JP 2021-533353 dated Aug. 2, 2022, in 5 pages.

\* cited by examiner

FIG. 5
(a) 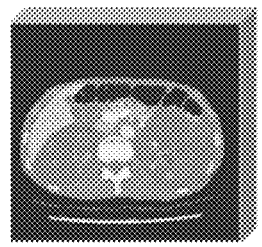 (b) 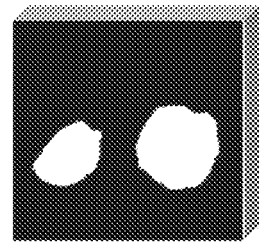

METHOD FOR MEASURING VOLUME OF ORGAN BY USING ARTIFICIAL NEURAL NETWORK, AND APPARATUS THEREFOR

The present application is a U.S. national phase application under 35 U.S.C. § 371 of International Application No. PCT/KR2019/017514, filed on Dec. 11, 2019, which claims the benefit of Korean Patent Application Nos. 10-2018-0158812 and 10-2019-0162842 filed on Dec. 11, 2018 and Dec. 9, 2019, respectively, in the Korean Intellectual Property Office, the entire disclosure of each of which is incorporated herein by reference.

TECHNICAL FIELD

The present disclosure relates to a method of measuring a volume of an organ by using an artificial neural network, and an apparatus for the method. In detail, the present disclosure relates to a method of detecting an organ region through an artificial neural network by using a 3D image of an organ and measuring a volume of the organ based on the detected organ region.

Embodiments disclosed in the present disclosure relate to a method of determining a progression state of a polycystic kidney or a polycystic liver and a technology for an electronic medical device for performing the method.

BACKGROUND ART

Accurate measurement of the volume of a kidney and a liver is a very important step for pathophysiology, analysis of treatment mechanisms, and evaluation of the effectiveness of therapeutic drugs. In particular, since a polycystic kidney has a characteristic of showing a variety of shapes that are anatomically inconsistent, it is very difficult to grasp the shape of the organ and only experts can determine the shape, and the task cannot be entrusted to ordinary workers even if it is a simple work. Performing a task on all of hundreds of CT image slides requires heavy labor of the doctors (repetition of simple labor), taking a very long time. Accordingly, through global multicenter research such as HALT-PKD cohort, CRISP, SUISSE study, etc., development of techniques for this problem is being actively carried out, but the scientific reliability of the volume of organs measured by each institution is currently only about 86%.

Polycystic kidney disease is a genetic disorder in which the kidney is transformed into a honeycomb shape due to multiple cysts filled with fluid. As the disease progresses, the cysts gradually replace normal tissues, the size of the kidney increases, and the function thereof gradually decreases, leading to end-stage renal failure. Some polycystic kidney diseases can also be accompanied by polycystic liver disease.

There are approximately 12.5 million people diagnosed with polycystic kidney disease worldwide, and the disease occurs in approximately one in 500 people. Polycystic kidney disease has been an incurable disease in the past, but has been receiving a lot of attention due to the recent development of new drugs.

DESCRIPTION OF EMBODIMENTS

Technical Problem

Embodiments of the present disclosure provide a method of accurately detecting an organ region by using an image acquired in a hospital and accurately measuring the volume of the organ, and an apparatus therefor.

Meanwhile, in the diagnosis of polycystic kidney disease or polycystic liver disease, it may be pathophysiologically or medically highly important to accurately measure the volume of the kidney or liver. For example, the pathophysiological hypothesis that depression of a renal function occurs due to an increase in the volume of the kidney and liver (pressure effect) has not yet been evaluated properly due to the practical reason that 'the volume of the liver cannot be accurately measured.' As another example, depending on the volume of the kidney or liver, the doctor may more accurately determine whether a patient has polycystic kidney disease or polycystic liver disease or the degree of progression of the disease.

Accurate measurement of the volume of a kidney or a liver will allow to clearly evaluate the above hypothesis related to the depression of the renal function and may be recognized as important research data for the functional evaluation of drugs to be released in the future. In addition, it can greatly contribute to enabling the doctor to determine an appropriate treatment point so that patients do not develop chronic renal failure.

Although there is a method of using a semi-automatic extraction program (2D stereology) to measure the volume of a kidney or liver, the purchase cost of the semi-automatic extraction program is as high as hundreds of millions of dollars, and the analysis time also takes one or two hours per patient. In addition, when using the semi-automatic extraction program, there may be a problem that additional labor costs are incurred.

In addition, although region extraction technology such as 2D stereology is a technology that has been attempted in various areas, since it is difficult to grasp the anatomy of the kidney or liver, the technical completion thereof may be relatively low. For example, the accuracy of area extraction of a kidney by using 2D stereology technology is reported to be about 86% at the maximum.

Various embodiments disclosed herein may provide a technique for solving the above problem.

Solution to Problem

A method of measuring a volume of an organ, according to an embodiment of the present disclosure includes: acquiring a plurality of captured images of the organ and photographing metadata and preprocessing the plurality of images to acquire a plurality of image patches of a specified size; inputting the plurality of image patches into a 3D CNN (Convolutional Neural Network)-based neural network model and estimating an organ region corresponding to each of the plurality of image patches; measuring a volume of the organ by using an area of the estimated organ region and the photographing metadata; measuring an uncertainty value of the neural network model and uncertainty values of the plurality of images based on a result of estimating by the neural network model; modifying at least one of the plurality of images based on the uncertainty values of the plurality of images; and modifying a labeling policy of the neural network model based on the uncertainty value of the neural network model.

According to an embodiment, the plurality of captured images of the organ may include a CT image acquired from a DICOM (Digital Imaging and Communications in Medicine) file and a labeling image with respect to the organ, and the photographing metadata may include pixel spacing data and image depth data with respect to each of the plurality of images.

According to an embodiment, the acquiring of the plurality of image patches may include performing data augmentation on a first image included in the plurality of images to generate a plurality of images from the first image and acquiring a plurality of image patches by preprocessing the generated, plurality of images, wherein the data augmentation includes one or more of spatial augmentation, color augmentation, noise augmentation, and cropping of the image.

According to an embodiment, the plurality of images may include a plurality of 3D images acquired by capturing images of the organ, and the acquiring of the plurality of image patches may include sliding in a depth direction with respect to the plurality of 3D images and acquiring the plurality of image patches of a specified size.

According to an embodiment, the neural network model may perform dropout in a learning operation and an inference operation, and the uncertainty value of the neural network model may be measured based on a variance value with respect to a probability distribution of resultant data in the inference operation of the neural network model.

According to an embodiment, the uncertainty values of the plurality of images may be measured based on an estimated variance value of the resultant data in the inference operation of the neural network model.

According to an embodiment, the modifying of at least one of the plurality of images based on the uncertainty values of the plurality of images may include: detecting one or more images in which the uncertainty values of the plurality of images are equal to or greater than a reference value; and modifying the detected image based on a user input with respect to the organ region of the detected image.

According to an embodiment, the method may further include training the neural network model by setting weights of the plurality of images according to the modified labeling policy and assigning, to the modified image, a greater weight than that assinged to a non-modified image.

An organ volume measuring apparatus according to another embodiment of the present disclosure includes a processor, wherein the processor is configured to acquire a plurality of captured images of the organ and photographing metadata and preprocess the plurality of images to acquire a plurality of image patches of a specified size; input the plurality of image patches into a 3D CNN (Convolutional Neural Network)-based neural network model and estimate an organ region corresponding to each of the plurality of image patches; measure a volume of the organ by using an area of the estimated organ region and the photographing metadata; measure an uncertainty value of the neural network model and uncertainty values of the plurality of images based on a result of estimating by the neural network model; modify at least one of the plurality of images based on the uncertainty values of the plurality of images; and modify a labeling policy of the neural network model based on the uncertainty value of the neural network model.

A method of measuring a volume of an organ, according to an embodiment of the present disclosure, includes: acquiring a plurality of captured images of the organ and photographing metadata and preprocessing the plurality of images to acquire a plurality of image patches of a specified size; inputting the plurality of image patches into a 3D CNN (Convolutional Neural Network)-based neural network model and estimating an organ region corresponding to each of the plurality of image patches; measuring a volume of the organ by using an area of the estimated organ region and the photographing metadata; measuring an uncertainty value of the neural network model and uncertainty values of the plurality of images based on a result of estimating by the neural network model; modifying at least one of the plurality of images based on the uncertainty values of the plurality of images; and modifying a labeling policy of the neural network model based on the uncertainty value of the neural network model.

According to an embodiment, the plurality of captured images of the organ may include a CT image acquired from a DICOM (Digital Imaging and Communications in Medicine) file and a labeling image with respect to the organ, and the photographing metadata may include pixel spacing data and image depth data with respect to each of the plurality of images.

According to an embodiment, the acquiring of the plurality of image patches may include performing data augmentation on a first image included in the plurality of images to generate a plurality of images from the first image and acquiring a plurality of image patches by preprocessing the generated, plurality of images, wherein the data augmentation includes one or more of spatial augmentation, color augmentation, noise augmentation, and cropping of the image.

According to an embodiment, the plurality of images may include a plurality of 3D images acquired by capturing images of the organ, and the acquiring of the plurality of image patches may include sliding in a depth direction with respect to the plurality of 3D images and acquiring the plurality of image patches of a specified size.

According to an embodiment, the neural network model may perform dropout in a learning operation and an inference operation, and the uncertainty value of the neural network model may be measured based on a variance value with respect to a probability distribution of resultant data in the inference operation of the neural network model.

According to an embodiment, the uncertainty values of the plurality of images may be measured based on an estimated variance value of the resultant data in the inference operation of the neural network model.

According to an embodiment, the modifying of at least one of the plurality of images based on the uncertainty values of the plurality of images may include: detecting one or more images in which the uncertainty values of the plurality of images are equal to or greater than a reference value; and modifying the detected image based on a user input with respect to the organ region of the detected image.

According to an embodiment, the method may further include training the neural network model by setting weights of the plurality of images according to the modified labeling policy and assigning, to the modified image, a greater weight than that assigned to a non-modified image.

An organ volume measuring apparatus according to another embodiment of the present disclosure includes a processor, wherein the processor is configured to acquire a plurality of captured images of the organ and photographing metadata and preprocess the plurality of images to acquire a plurality of image patches of a specified size; input the plurality of image patches into a 3D CNN (Convolutional Neural Network)-based neural network model and estimate an organ region corresponding to each of the plurality of image patches; measure a volume of the organ by using an area of the estimated organ region and the photographing metadata; measure an uncertainty value of the neural network model and uncertainty values of the plurality of images based on a result of estimating by the neural network model;

modify at least one of the plurality of images based on the uncertainty values of the plurality of images; and modify a labeling policy of the neural network model based on the uncertainty value of the neural network model.

BRIEF DESCRIPTION OF DRAWINGS

FIG. 5 is a diagram illustrating an example of neural network input data according to an embodiment of the present disclosure.

MODE OF DISCLOSURE

Figure 1:
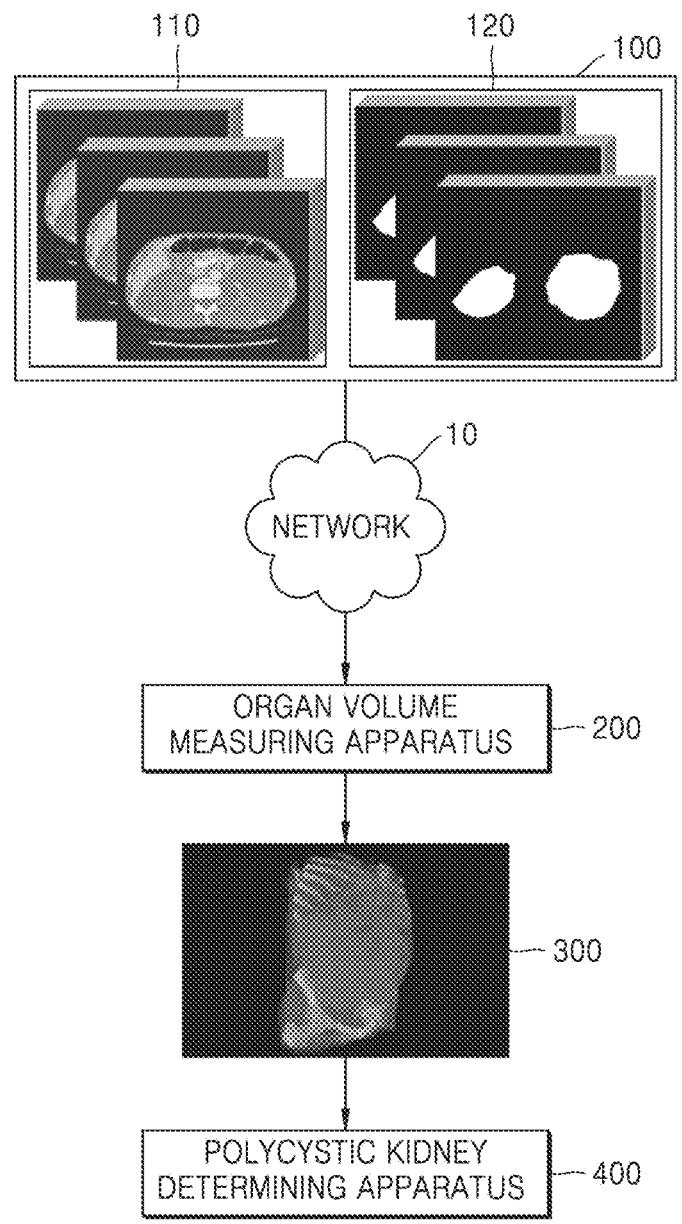
FIG. 1 is a diagram showing an example of a system for determining a polycystic kidney including an organ volume measuring apparatus according to an embodiment of the present disclosure.

The present disclosure will now be described more fully with reference to the accompanying drawings, in which exemplary embodiments of the present disclosure are shown. The embodiments will be described in detail such that one of ordinary skill in the art may easily work the present disclosure. It should be understood that the embodiments of the present disclosure may vary but do not have to be mutually exclusive. For example, particular shapes, structures, and properties according to a predetermined embodiment described in this specification may be modified in other embodiments without departing from the spirit and scope of the present disclosure. In addition, positions or arrangement of individual components of each of the embodiments may also be modified without departing from the spirit and scope of the present disclosure. Accordingly, the detailed description below should not be construed as having limited meanings but construed to encompass the scope of the claims and any equivalent ranges thereto. In the drawings, like reference numerals denote like elements in various aspects.

Hereinafter, the present disclosure will now be described more fully with reference to the accompanying drawings, in which exemplary embodiments of the present disclosure are shown such that one of ordinary skill in the art may easily work the present disclosure.

A system for determining a polycystic kidney, the system including an organ volume measuring apparatus, according to an embodiment of the present disclosure, will now be described in detail.

Artificial intelligence (AI) disclosed in the present disclosure may refer to a field of researching artificial intelligence or a methodology to create artificial intelligence. Machine learning, which is a field of artificial intelligence technology, may be an algorithm that allows a computer to analyze data by using a technical method in which a computing device learns through data to understand a specific object or condition, or finds and classifies a pattern of data. Machine learning disclosed in the present disclosure may be understood as a concept including an operating method for training an artificial intelligence model.

Hereinafter, a neural network model according to some embodiments of the present disclosure may be determined through a Neural Architecture Search (NAS) algorithm. The Neural Architecture Search is a method of designing a structure of an artificial neural network through deep learning. For example, an optimal artificial neural network structure may be searched by learning a neural network derived through a recurrent neural network. In detail, in a neural network model according to some embodiments of the present disclosure, metadata such as a filter size and a stride for each layer included in the neural network model may be determined by the NAS algorithm. It is to be noted that the above-described NAS algorithm includes all of various types of algorithms that can be modified and designed by a person skilled in the art, and for example, the NAS algorithm includes algorithms such as SC-NAS and C-NAS.

An organ volume measuring apparatus 200 according to an embodiment may use, as input data 100, a plurality of images 110 which are captured images of an organ and a plurality of images 120 displaying an organ region. The organ volume measuring apparatus 200 may receive the input data 100 from an external server through a network 10. In this case, the external server is, for example, a hospital server, and the organ volume measuring apparatus 200 may acquire the input data 100, which is a standard medical image format, from the hospital server. In this case, the input data 100 including a plurality of images of organs included in the input data 100 may be in a DICOM (Digital Imaging and Communications in Medicine) format, and may include CT images, patient information, measurement data and photographing information. However, this is merely an example, and the input data 100 according to some embodiments of the present disclosure may also be in the form of various image files such as JPG, PNG, and TIF. In an embodiment, the input data 100 may include 3D image data, and in this case, each voxel constituting a volume of an image may be in the form of a pixel arrangement. In addition, the plurality of images 120 displaying an organ region and included in the input data 100 may be correct answer data indicating organ regions to be detected using an artificial neural network. That is, the plurality of images 120 displaying an organ region may be annotation data (or labeling data) with respect to the organ region. An artificial neural network that detects an organ region according to some embodiments of the present disclosure by using the above-described input data 100 may perform supervised learning.

The organ volume measuring apparatus 200 that has received the input data 100 may detect an organ region included in each image by using a 3D CNN-based artificial neural network. By using s 3D CNN-based neural network rather than the one based on 2D CNN, CT data acquired in the form of 3D images may be accurately analyzed. However, by performing an additional preprocessing process by a person skilled in the art, a method of measuring a volume of an organ according to some embodiments of the present disclosure may also be performed using a 2D CNN-based neural network. In detail, the organ volume measuring apparatus 200 may acquire a plurality of captured images of an organ and photographing metadata and preprocess the plurality of images to acquire a plurality of image patches of a specified size, input the plurality of image patches into a 3D CNN (Convolutional Neural Network)-based neural network model and estimate an organ region corresponding to each of the plurality of image patches, measure a volume of the organ by using an area of the estimated organ region and the photographing metadata, measure an uncertainty value of the neural network model and uncertainty values of the plurality of images based on a result of estimating by the neural network model, modify at least one of the plurality of images based on an uncertainty value of input data, and modify a labeling policy of the neural network model based on the uncertainty value of the neural network model.

In addition, data about an organ region detected according to an embodiment may be used to generate a 2D image or a 3D model 300 corresponding to the organ and displayed on a display. In this case, the data about the detected organ region may be modified in response to a user input with respect to the 2D image or 3D model 300 displayed on the display, and the modified data may be used again as input data of an artificial neural network.

Next, a polycystic kidney determining apparatus 400 may measure a polycystic kidney by using volume data of the organ region. However, this is merely a use example in the case when the detected organ region is a kidney or liver, and the disease or symptom to be identified may vary according to the detected organ region according to some embodiments of the present disclosure.

Hereinafter, an internal configuration of the organ volume measuring apparatus 200 will be described in detail with reference to FIG. 2.

In an embodiment, the organ volume measuring apparatus 200 for measuring a volume of an organ may include an input/output interface 201, a memory 202, a processor 203, and a communication module 204. The memory 202 may be a computer-readable recording medium and may include a permanent mass storage device such as random access memory (RAM), read only memory (ROM), and a disk drive. In addition, the memory 202 may temporarily or permanently store program codes and settings for controlling the organ volume measuring apparatus 200, a camera image, and pose data of an object.

The processor 203 may be configured to process an instruction of a computer program by performing basic arithmetic, logic, and input/output operations. An instruction may be provided to the processor 203 by the memory 202 or the communication module 204. For example, the processor 203 may be configured to execute an instruction received according to a program code stored in a recording device such as the memory 202.

The communication module 204 may provide a function for communicating with an external server through the network 10. The external server described above may be, for example, a hospital server that provides medical images. For example, a request generated by the processor 203 of the organ volume measuring apparatus 200 according to a program code stored in a recording device such as the memory 202 may be transmitted to an external server through the network 10 under the control by the communication module 204. Conversely, a control signal, an instruction, content, a file, or the like provided under the control by a processor of an external server may be received by the organ volume measuring apparatus 200 through the communication module 204 via the network 10. For example, a control signal or an instruction of an external server, received through the communication module 204, may be transmitted to the processor 203 or the memory 202, and contents or files may be stored in a storage medium that may be further included in the organ volume measuring apparatus 200. Further, a communication method of the communication module 204 is not limited, but the network 10 may be a wireless local area network. For example, the network 10 may be a Bluetooth, BLE (Bluetooth Low Energy) or a WiFi communication network.

Also, the input/output interface 201 may receive a user input and display output data. The input/output interface 201 according to an embodiment may display a 2D image or a 3D model corresponding to an organ on a display. Alternatively, feedback information with respect to a detected organ region may be received from a user.

Although not illustrated, the organ volume measuring apparatus 200 according to an embodiment may further include a camera module. The camera module may be a camera module including one or more individual cameras. For example, the camera module may be a camera module built in the organ volume measuring apparatus 200 or may be a module connected to a separately included camera device. In this case, a captured image of an organ acquired from the camera module may be stored in the memory 202 or a storage medium further included in the organ volume measuring apparatus 200.

Figure 2:
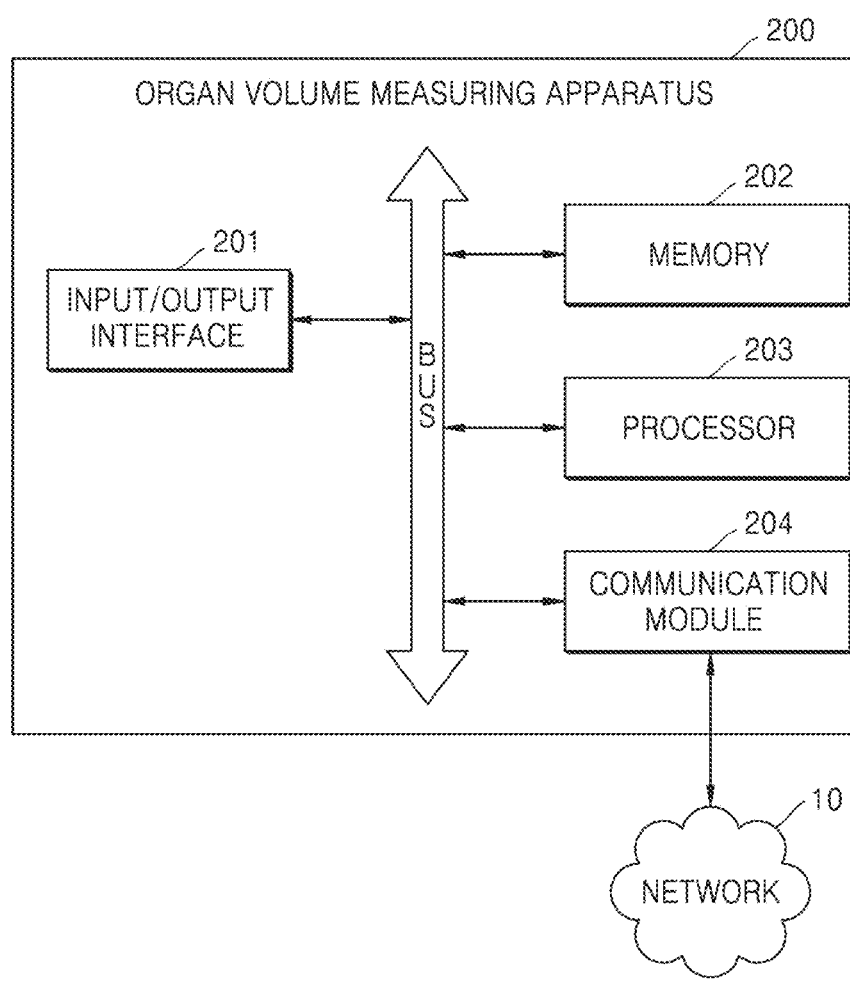
FIG. 2 is a hardware structural diagram illustrating an internal configuration of an organ volume measuring apparatus for measuring the volume of an organ of an object according to an embodiment of the present disclosure.

In addition, in other embodiments, the organ volume measuring apparatus 200 may include more components than those of FIG. 2. However, there is no need to clearly illustrate most of the components of the related art. For example, the organ volume measuring apparatus 200 may include a battery and a charging device that supply power to internal components of a user terminal, and may be implemented to include at least some of the above-described input/output devices or may further include other components such as a transceiver, a GPS (Global Positioning System) module, various sensors, and a database.

Figure 3:
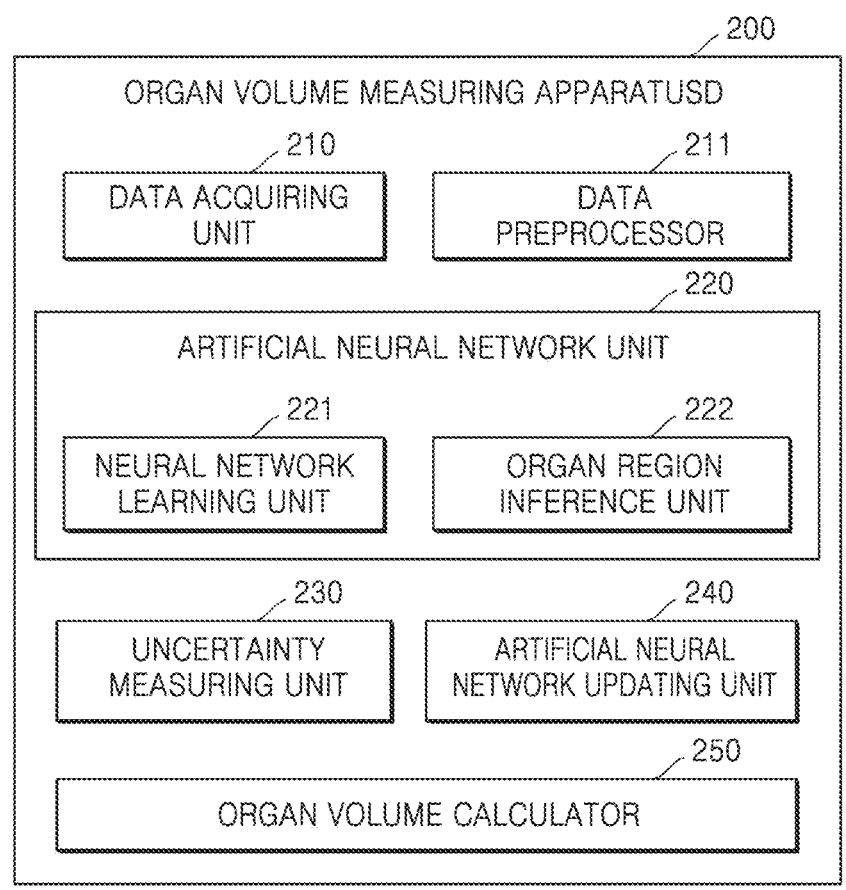
FIG. 3 is a hardware block diagram for describing a configuration and operation of an organ volume measuring apparatus according to an embodiment of the present disclosure.

FIG. 3 is a hardware block diagram for describing a configuration and operation of the organ volume measuring apparatus according to an embodiment of the present disclosure.

In an embodiment, the organ volume measuring apparatus 200 may include a data acquiring unit 210, a data preprocessor 211, an artificial neural network unit 220, an uncertainty measuring unit 230, an artificial neural network updating unit 240, and an organ volume calculator 250.

In an embodiment, the data acquiring unit 210 may acquire a plurality of captured images of an organ and photographing metadata. The plurality of images of the organ may include a CT image acquired from a DICOM (Digital Imaging and Communications in Medicine) file and a labeling image of the organ. However, this is merely an example, and the input data 100 according to some embodiments of the present disclosure may also be in the form of various image files such as JPG, PNG, and TIF. The labeling image is an image in which an organ region is displayed, and may be correct answer data with respect to an organ region to be estimated through an artificial neural network. Accordingly, an artificial neural network estimating an organ region, according to some embodiments of the present disclosure, may perform supervised learning by using the labeling data described above.

In an embodiment, the data preprocessor 211 may perform data augmentation to secure sufficient data necessary for learning of an artificial neural network. In addition, in an embodiment, the data preprocessor 211 may preprocess a plurality of images to acquire a plurality of image patches having a specified size. In an embodiment, the data preprocessor 211 augmenting learning data may perform at least one of spatial augmentation, color augmentation, noise augmentation, and cropping. In addition, the data preprocessor 211 generating a plurality of image patches may perform image resizing for generating a plurality of image patches having the same size and image patch extraction in a form suitable for an artificial neural network. In addition, in an embodiment, the data preprocessor 211 may slide a 3D CT image in a depth direction to acquire a plurality of image patches.

In an embodiment, the artificial neural network unit 220 may include a neural network learning unit 221 and an organ region inference unit 222. In an embodiment, the artificial neural network unit 220 may perform a learning operation and an inference operation by using an artificial neural network based on a 3D CNN (Convolutional Neural Network). In an embodiment, the neural network learning unit 221 may perform learning of the above-described artificial neural network by using image patches generated based on a plurality of CT images and a plurality of labeling images acquired using the data acquiring unit 210. In addition, in an embodiment, the organ region inference unit 222 may infer an organ region corresponding to each image patch by using a plurality of image patches generated based on a plurality of CT images.

Meanwhile, the above-described 3D CNN-based artificial neural network according to some embodiments of the present disclosure may perform dropout to prevent the problem of overfitting. According to an embodiment, the above-described artificial neural network may perform dropout in both the learning operation and the inference operation. In this case, the artificial neural network may randomly perform an inference operation based on a sample of a probability distribution.

In an embodiment, the uncertainty measuring unit 230 may measure uncertainty values of input data and an artificial neural network model. The uncertainty values of the input data and the artificial neural network model refer to numerical values indicating whether a specific cause of the input data and the artificial neural network model, in which an error has occurred, can be searched. Accordingly, the uncertainty measuring unit 230 according to the embodiment may measure an uncertainty value of a neural network model due to insufficient data or a structure that prevents analysis of all data. In this case, the uncertainty measuring unit 230 may measure the uncertainty value of the neural network based on a variance value regarding a probability distribution of resultant data in the inference operation of the artificial neural network model described above. In addition, the uncertainty measuring unit 230 according to the embodiment may measure an uncertainty value of data due to a case in which different labelings are performed due to randomness data even though the uncertainty value is the same. In this case, the uncertainty measuring unit 230 may measure uncertainty values of a plurality of images based on an estimated variance value of the resultant data in the inference operation of the artificial neural network model described above.

In an embodiment, the artificial neural network updating unit 240 may modify the organ region estimated by the organ region inference unit 222 with respect to each of the plurality of images. In detail, the artificial neural network updating unit 240 may correct an organ region detected from an image, based on uncertainty of the artificial neural network model. In this case, the organ volume measuring apparatus 200 may acquire, from the user, information on the modified organ region by using an input/output interface.

In addition, the artificial neural network updating unit 240 may modify a labeling policy of the above-described artificial neural network model based on an uncertainty value of input data. In addition, the artificial neural network updating unit 240 may set a weight of each of the plurality of images according to the modified labeling policy, and assign a larger weight to an image in which the estimated organ region is modified than other images and use the image as learning data of the artificial neural network.

In an embodiment, the organ volume calculator 250 may estimate a volume of an organ by using an area of an organ region estimated using the artificial neural network unit 220 with respect to each of a plurality of image patches and photographing metadata with respect to a plurality of images.

Figure 4:
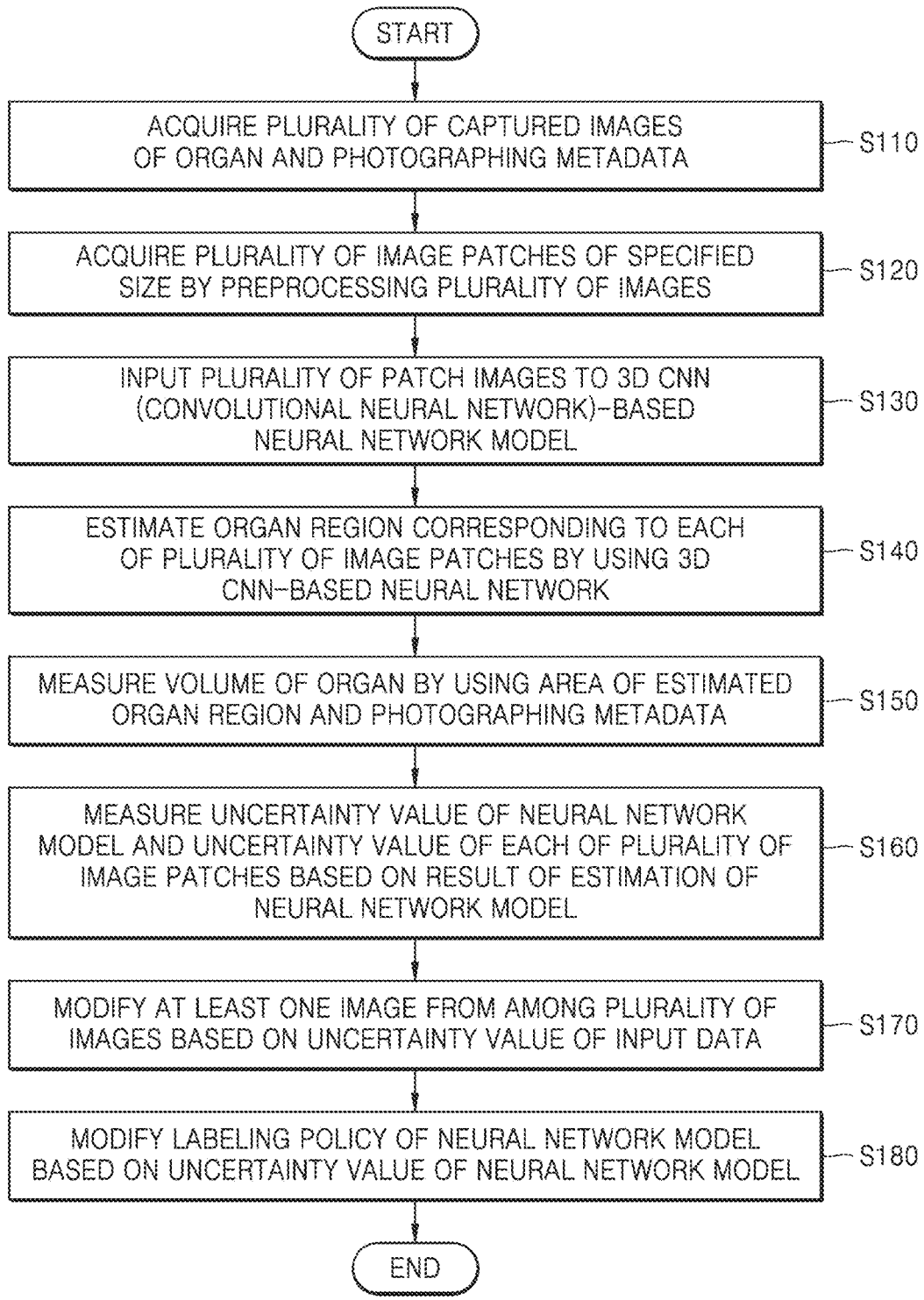
FIG. 4 is a flowchart of a method of measuring a volume of an organ according to an embodiment of the present disclosure.

FIG. 4 is a flowchart of a method for measuring a volume of an organ according to an embodiment of the present disclosure.

In operation S110, an organ volume measuring apparatus may acquire a plurality of captured images of an organ and photographing metadata.

The plurality of images of the organ may include a CT image acquired from a DICOM (Digital Imaging and Communications in Medicine) file and a labeling image with respect to the organ. However, this is merely an example, and the input data 100 according to some embodiments of the present disclosure may also be in the form of various image files such as JPG, PNG, and TIF. In addition, the photographing metadata may include pixel spacing data with respect to each of the plurality of images and depth data of an image slice. In an embodiment, the plurality of images described above may be a plurality of 3D captured images of the organ. The labeling image is an image in which an organ region is displayed, and may be correct answer data with respect to an organ region to be estimated through an artificial neural network. Accordingly, an artificial neural network estimating an organ region according to some embodiments of the present disclosure may perform supervised learning by using the labeling data described above. Detailed description thereof will be given later with reference to FIG. 5.

In operation S120, the organ volume measuring apparatus may preprocess the plurality of images to acquire a plurality of image patches having a specified size.

In detail, the organ volume measuring apparatus may perform data augmentation on each of the plurality of images to generate a plurality of images, and acquire a plurality of image patches by preprocessing the generated plurality of images. In an embodiment, the organ volume measuring apparatus may perform data augmentation when learning data is insufficient. In this case, the organ volume measuring apparatus may perform one or more of spatial augmentation, color augmentation, noise augmentation, and cropping. In an embodiment, spatial augmentation may include at least one of mirroring of each of a plurality of images, channel transformation for simulation of registration errors, elastic deformation, rotation, scaling, and resampling. However, it should be noted that this is merely an example of spatial augmentation, and embodiments according to the present disclosure are not limited thereto. In an embodiment, color augmentation may include at least one of addition of brightness, multiplication of brightness, contrast adjustment, and gamma adjustment. However, it should be noted that this is merely an example of color augmentation, and embodiments according to the present disclosure are not limited thereto. In an embodiment, in noise augmentation, at least one of Gaussian noise and Rician noise may be used. However, it should be noted that this is merely an example of noise augmentation, and embodiments according to the present disclosure are not limited thereto. In an embodiment, cropping may be one of random cropping and center cropping. However, it should be noted that this is merely an example of cropping, and embodiments according to the present disclosure are not limited thereto.

In addition, the organ volume measuring apparatus may perform image resizing for generating a plurality of image patches having the same size and extracting of an image patch in a form suitable for an artificial neural network. In addition, in an embodiment, the organ volume measuring apparatus may slide a 3D CT image in a depth direction to acquire a plurality of image patches. In addition, the organ volume measuring apparatus may generate a plurality of image patches by performing overlapping on a predetermined patch size by a specified ratio. In addition, the organ volume measuring apparatus may add padding for generating an image patch of a specified size in order to prevent reduction in a size of data through a convolution operation. For example, the organ volume measuring apparatus may add symmetric padding with respect to a width and/or height, and may add zero padding with respect to a depth to match a form of input data of a 3D CNN-based artificial neural network. In this case, added padding data may be '0' data. Detailed description thereof will be given later with reference to FIGS. 6 through 8.

In operation S130, the organ volume measuring apparatus may input a plurality of image patches into a 3D CNN (Convolutional Neural Network)-based neural network model. The neural network model may perform dropout in a learning operation and an inference operation to prevent the occurrence of the problem of overfitting. In addition, the neural network model according to an embodiment may include an encoding layer including a reduction cell and a decoding layer including an expansion cell. Detailed description thereof will be given later with reference to FIGS. 9 and 10.

In operation S140, the organ volume measuring apparatus may estimate an organ region corresponding to each of the plurality of image patches by using the 3D CNN-based neural network. According to an embodiment, the artificial neural network estimating an organ region may estimate the organ region with respect to each of the plurality of image patches. In addition, the organ volume measuring apparatus may further perform data post-processing on resultant data. For example, the organ volume measuring apparatus may perform at least one of depth spline, depth stitching, and unpadding. In an embodiment, the organ volume measuring apparatus may perform a depth spline on the resultant data to assign a lower inference weight to an image as a distance from a center of each image patch increases. Accordingly, a natural stitching result may be acquired using the resultant data. In addition, in an embodiment, the organ volume measuring apparatus may configure a new volume by performing depth stitching on resultant data corresponding to each of the plurality of image patches. In addition, in an embodiment, the organ volume measuring apparatus may perform un-padding to control padding added in a data preprocessing operation.

In operation S150, the organ volume measuring apparatus may measure a volume of the organ by using the area of the estimated organ region and photographing metadata. In detail, the organ volume measuring apparatus may calculate the volume of the organ by using a spacing of pixels included in the photographing metadata, a thickness of an image slice, and the number of voxels included in the image patches. Detailed description thereof will be given later with reference to FIG. 11.

In operation S160, the organ volume measuring apparatus may measure an uncertainty value of the neural network model and an uncertainty value of each of the plurality of image patches based on a result of estimation of the neural network model. In an embodiment, the uncertainty value of the neural network model may be measured based on a variance value with respect to a probability distribution of resultant data in the inference operation of the neural network model. Also, the uncertainty value of each of the plurality of image patches may be measured based on a variance estimate value of the resultant data in the inference operation of the neural network model.

In operation S170, the organ volume measuring apparatus may modify at least one image from among the plurality of images based on the uncertainty value of the neural network model. The organ volume measuring apparatus may select data that needs to be modified based on the uncertainty value of the neural network model. In addition, the organ volume measuring apparatus may establish a label policy based on an uncertainty value of input data. Accordingly, the neural network model according to some embodiments of the present disclosure may update the neural network model (active learning) by using the corrected data. That is, the organ volume measuring apparatus may detect one or more images having an uncertainty value of input data, the uncertainty value being equal to or greater than a reference value, and modify the detected image based on a user input with respect to the organ region of the detected image.

In operation S180, the organ volume measuring apparatus may modify a labeling policy of the neural network model based on the uncertainty value of the input data. The organ volume measuring apparatus according to an embodiment may perform labeling on each piece of input data according to the modified labeling policy, and may train the neural network model by assigning, to input data having a label that is modified, a greater weight than that assigned to input data having a label that is not modified.

FIG. 5 is a diagram illustrating an example of neural network input data according to an embodiment of the present disclosure.

(a) is image data of a captured image of an organ, and a plurality of pieces of image data such as (a) may be acquired from a DICOM (Digital Imaging and Communications in Medicine) file. However, this is merely an example, and the input data 100 according to some embodiments of the present disclosure may also be in the form of various image files such as JPG, PNG, and TIF. In addition, in an embodiment, the organ volume measuring apparatus may further acquire photographing metadata about each of a plurality of images from a DICOM file. The photographing metadata may further include, for example, information on a size of each pixel of each of the plurality of images, depth information of an image, information about a size and the number of voxels.

(b) denotes data showing an organ region. (b) is correct answer data regarding an organ region to be inferred through an artificial neural network, and may be labeling data in which the organ region is labeled. The neural network model according to an embodiment may perform supervised learning by using the labeling data as shown in (b). However, in another embodiment, the neural network model detecting an organ region may also perform un-supervised learning by using only an image such as (a).

FIGS. 6 through 9 are diagrams for describing a method of preprocessing input data, according to an embodiment of the present disclosure.

Figure 6:
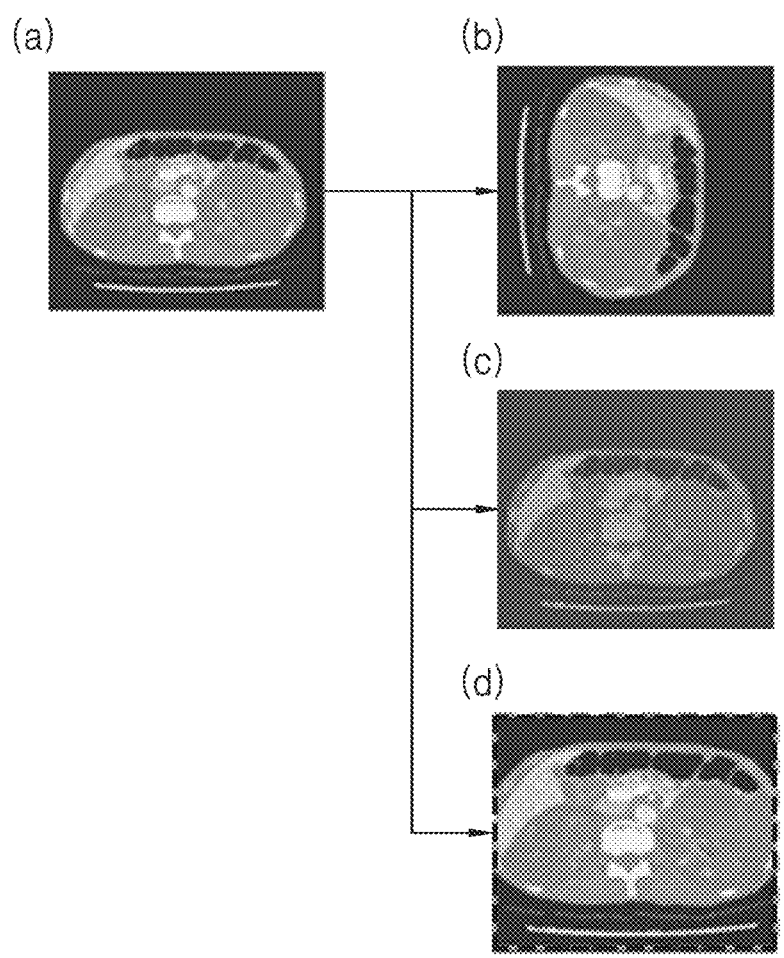
FIGS. 6 through 8 are diagrams for describing a method of preprocessing input data, according to an embodiment of the present disclosure.

Referring to FIG. 6, in an embodiment, the organ volume measuring apparatus may perform data augmentation to secure a sufficient amount of learning data. The organ volume measuring apparatus may perform one or more of spatial augmentation, color augmentation, noise augmentation, and cropping. In an embodiment, the spatial augmentation may include at least one of mirroring of each of a plurality of images, channel transformation for simulation of registration errors, elastic deformation, rotation, scaling, and resampling. In an embodiment, color augmentation may include at least one of addition of brightness, multiplication of brightness, contrast adjustment, and gamma adjustment. In an embodiment, in noise augmentation, at least one of Gaussian noise and Rician noise may be used. In an embodiment, cropping may be one of random cropping and center cropping. For example, an image shown in (b) is an example obtained by performing rotation with respect to (a), an image shown in (c) is an example of lowering a brightness of (a), and an image shown in (d) is an example obtained by performing center cropping. As described above, the organ volume measuring apparatus according to an embodiment may acquire a sufficient amount of learning data required for an artificial neural network, by transforming an acquired image in various ways.

Figure 7:
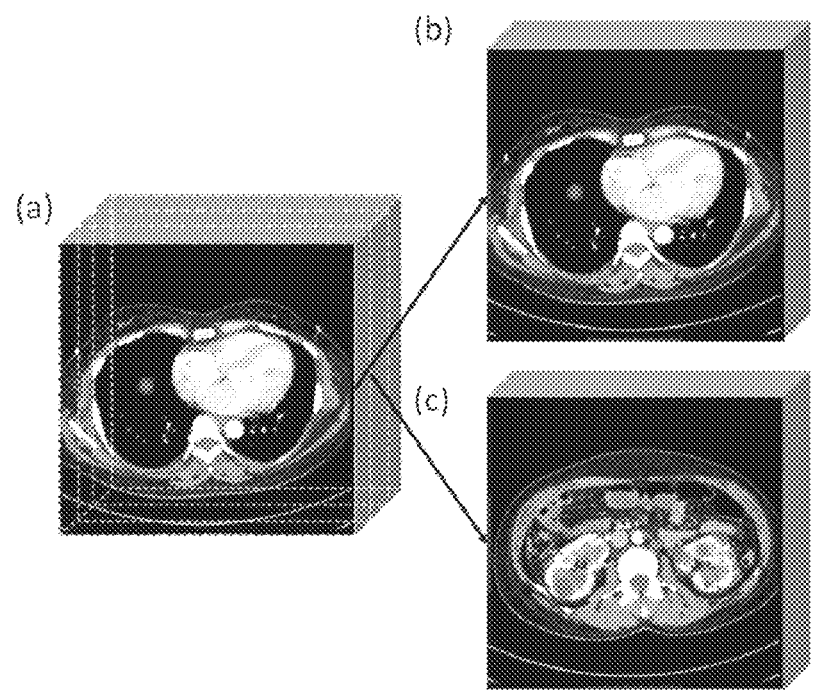

In addition, referring to FIG. 7, in an embodiment, the organ volume measuring apparatus may perform a data preprocessing process for acquiring an image patch of a specified size. First, the organ volume measuring apparatus may extract an image patch at the same scale by adjusting sizes of a plurality of images. Thereafter, the organ volume measuring apparatus may extract a 3D image of a specified size by scanning in one direction through a 3D sliding window. In an embodiment, the organ volume measuring apparatus may extract a plurality of image patches by overlapping a specified ratio of a specified patch size. For example, (b) and (c) are examples of 3D image patches extracted from (a).

Figure 8:
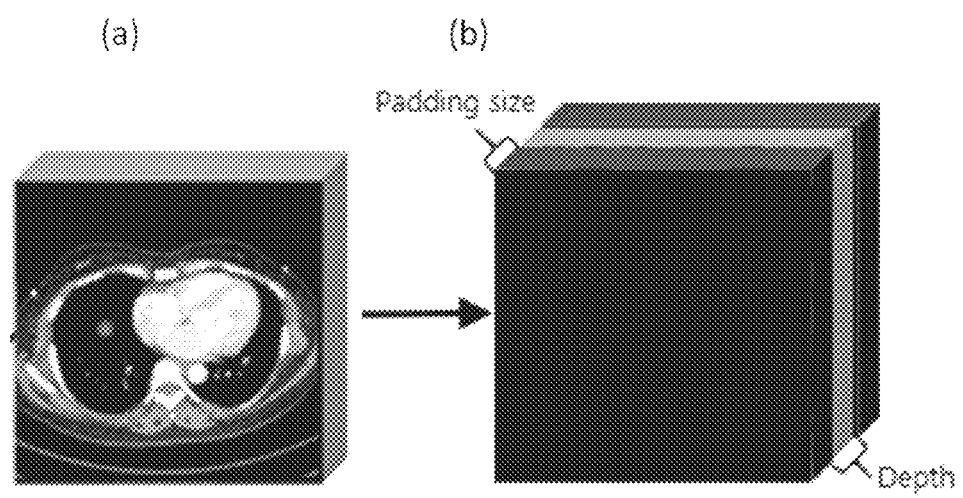

Referring to FIG. 8, the organ volume measuring apparatus according to an embodiment may add padding to input data in order to adjust a size regarding resultant data of an artificial neural network. An artificial neural network for estimating an organ region according to some embodiments of the present disclosure may be a 3D CNN-based model. Therefore, as an operation in the neural network is performed, a plurality of convolutional operations are performed on input data, and the size of the resultant data is inevitably reduced. Accordingly, the organ volume measuring apparatus may add padding with respect to width, height, and depth to acquire an image patch of a specified size. For example, FIG. (b) is an example of data in which padding with respect to depth is added with respect to (a). The present disclosure is not limited thereto, and an image patch to which padding is added according to some embodiments of the present disclosure may be an image in which a specific image is duplicated in a symmetrical form. In an embodiment, when padding of a specified size is added, the added data may be '0'. For example, padding in a depth direction may be added to a 2D image to be used as input data of a 3D CNN-based neural network. In this case, padding having a specified depth may include '0'. In another embodiment, the size of added padding may be '0'. As described above, as the neural network model according to some embodiments of the present disclosure uses a 3D image as input data, depth information may be added formally to the input data, and in this case, the depth may be '0'.

Figure 9:
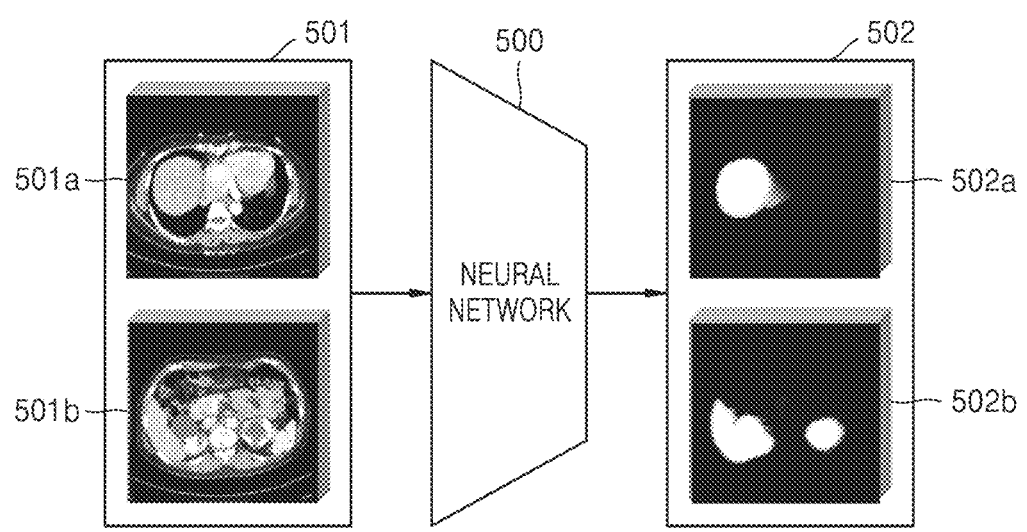
FIGS. 9 and 10 are diagrams for describing a structure of an artificial neural network according to an embodiment of the present disclosure.
Figure 10:
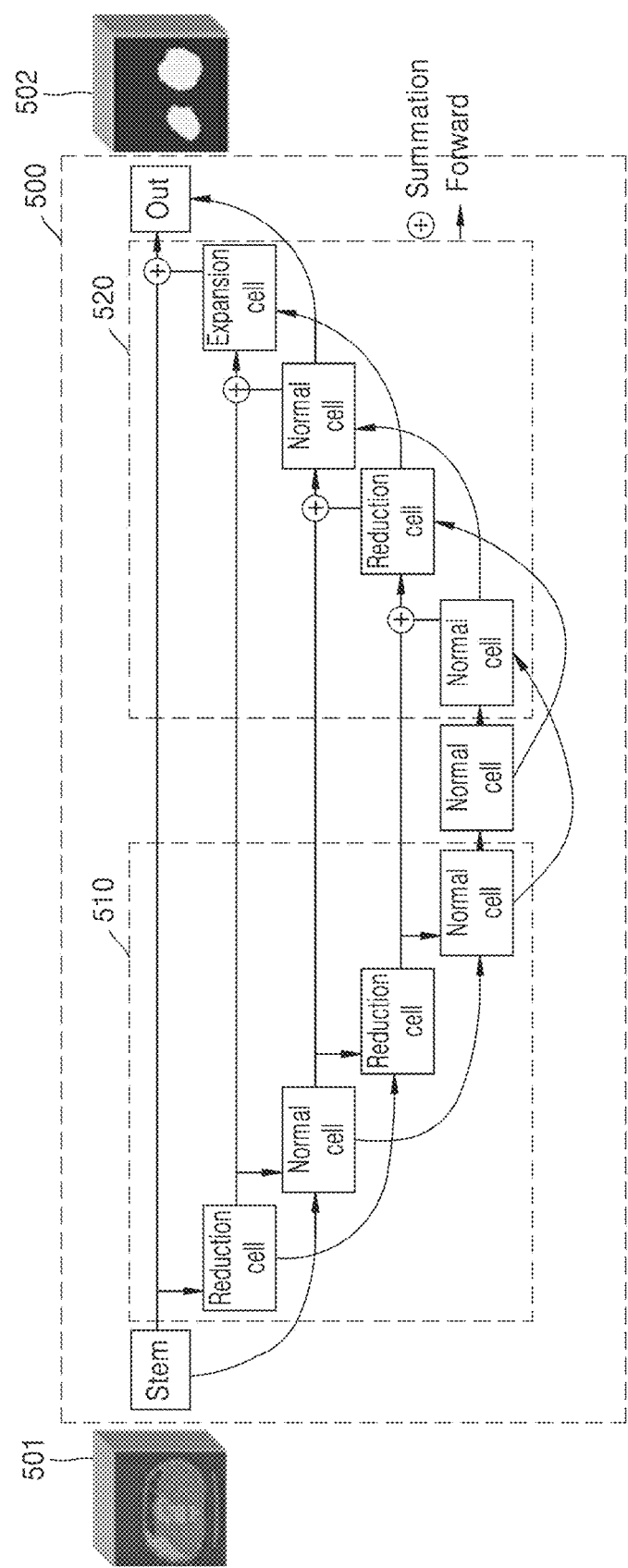

FIGS. 9 and 10 are diagrams for describing a structure of an artificial neural network according to an embodiment of the present disclosure.

Referring to FIG. 9, a neural network 500 receiving, as an input, first and second image patches 501a and 501b generated based on a plurality of images may extract organ regions 502a and 502b respectively corresponding to the image patches. For example, the organ region 502a corresponding to the first image patch 501a may be detected based on the first image patch 501a, and the organ region 502b corresponding to the second image patch 501b may be extracted based on the second image patch 501b.

In addition, in an embodiment, the organ volume measuring apparatus may measure an uncertainty value with respect to a neural network model and input data. Uncertainty in a model is caused due to lack of data or a neural network of a structure in which it is difficult to express all data. Accordingly, the artificial neural network model according to some embodiments of the present disclosure may perform dropout in a learning operation and an inference operation to prevent the occurrence of the problem of overfitting. In detail, the organ volume measuring apparatus may perform random prediction based on a sample of a probability distribution, and may perform the above-described random prediction by sampling k thinned neural nets and using an average value of each prediction value. In this case, the probability distribution may be a probability distribution of resultant data acquired in the inference operation of the neural network model, an average value at this time may be acquired as a predicted value, and a variance value at this time may be regarded as an uncertainty value.

Uncertainty of input data arises from the randomness that occurs in the process of generating data. In detail, for example, in a case where uncertainty values of first data and second data included in randomness data that is difficult to express with a probability are equal, even though the uncertainty values of the first data and the second data are equal, as the first data and the second data are not data acquired according to a specified probability, different labels may be applied to the first data and the second data When uncertainty of input data occurs as described above, the organ volume measuring apparatus according to some embodiments of the present disclosure may measure the above-described uncertainty value of the input data through variance estimation.

FIG. 10 is an exemplary diagram of a structure of an artificial neural network model according to an embodiment of the present disclosure.

In an embodiment, the neural network model 500 for extracting an organ region may be a 3D CNN-based neural network model, and may include an encoding layer 510 including a reduction cell and a decoding layer 520 including an expansion cell. However, it should be noted that the structure of the neural network model according to some embodiments of the present disclosure is not limited to that shown in FIG. 10 and may have various structures that can be adopted and modified by a person skilled in the art. In addition, the neural network model according to an embodiment of the present disclosure is not limited thereto, and an organ volume measuring method according to some embodiments of the present disclosure may also be performed by using a 2D CNN-based neural network by performing an additional preprocessing process by a person skilled in the art to perform.

Figure 11:
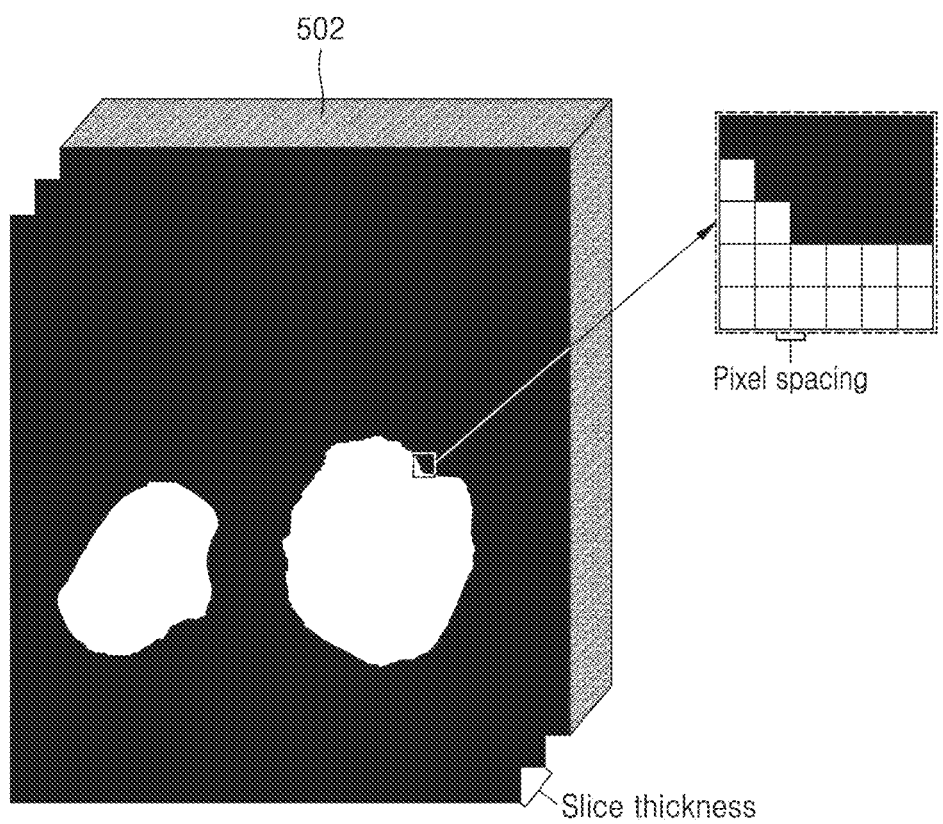
FIG. 11 is a view for describing a method of measuring a volume of an organ by using an organ region detected according to an embodiment of the present disclosure.

FIG. 11 is a view for describing a method of measuring a volume of an organ by using an organ region detected according to an embodiment of the present disclosure.

According to an embodiment, a volume of an organ to be photographed may be measured using resultant data of a neural network for detecting an organ region. An organ volume measuring apparatus may measure a volume of an organ by using an area of an estimated organ region and photographing metadata. In detail, the organ volume measuring apparatus may calculate the volume of the organ by using a spacing of pixels included in the photographing metadata, a thickness of an image slice, and the number of voxels included in an image patch. Referring to FIG. 11, for example, assuming that a spacing (or size) of square-shaped pixels is 0.6 mm, a thickness of an image slice is 1 mm, and the number of voxels is 2,000,000, the volume of the organ may be 0.6*0.6*1*2,000,000=0.36 mm$^2$*2,000,000=720 ml. As another example, an x-coordinate of a voxel.

Figure 12:
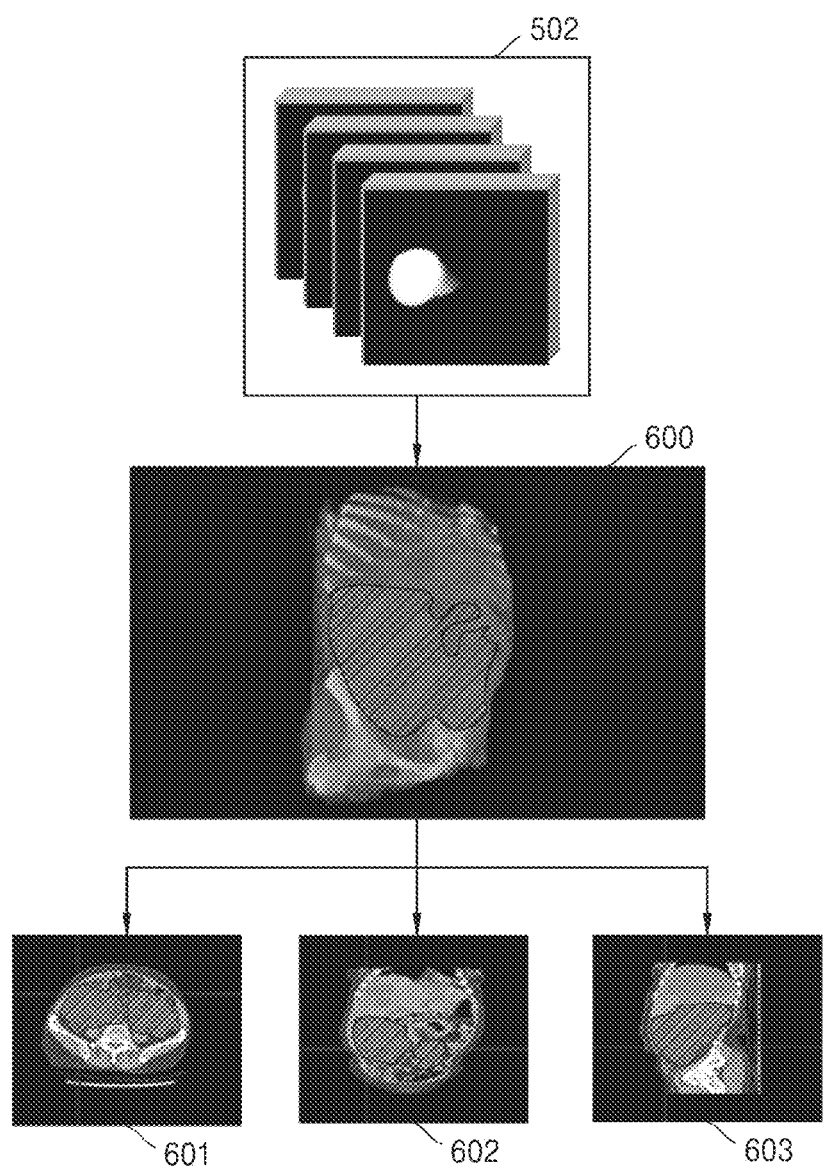
FIG. 12 is a diagram for describing a method of updating input data, according to an embodiment of the present disclosure.

FIG. 12 is a diagram for describing a method of updating input data, according to an embodiment of the present disclosure.

In an embodiment, by using data 502 about a plurality of organ regions estimated using a plurality of image patches, a 3D model 600 of a corresponding organ region may be generated. In an embodiment, the organ volume measuring apparatus may display the data 502 about the organ region or the 3D model 600 of the organ region described above. Next, the organ volume measuring apparatus may modify at least one image among a plurality of images based on an uncertainty value of an artificial neural network model. That is, the organ volume measuring apparatus may select data 601, 602, and 603 that needs to be modified based on the uncertainty value of the artificial neural network model. That is, the organ volume measuring apparatus may detect one or more images having an uncertainty value of input data, the uncertainty value being equal to or greater than a reference value, and modify the detected image based on a user input with respect to the organ region of the detected image. Also, the organ volume measuring apparatus may modify a labeling policy of the neural network model based on the uncertainty value of the input data. The organ volume measuring apparatus according to an embodiment may perform labeling on each piece of input data according to the modified labeling policy, and may train the neural network model by assigning, to input data having a label that is modified, a greater weight than that assigned to input data having a label that is not modified. Accordingly, the neural network according to some embodiments of the present disclosure may perform update of the neural network model (active learning) based on the modified data and a new labeling policy.

In addition, the organ volume measuring apparatus according to an embodiment of the present disclosure may verify the effect of a drug by using the organ volume measuring method described above. For example, a volume of the kidney and/or liver of a patient may be measured to conduct diagnosis of polycystic kidney and to determine a therapeutic effect according to drug administration. In detail, first, kidney volume segmentation of the kidney of a patient may be performed using the above-described artificial neural network for estimating an organ region. Then, kidney volume segmentation is performed by receiving patient data before and after administration, and then the volume of the kidney is measured. In this case, it is obvious that a volume of the kidney may be measured using a size of pixels and a thickness of an image slice included in a DICOM file regarding the kidney region of the patient. The efficacy of the drug may be measured based on a volume increase/decrease rate of the kidney measured according to the above-described method. Furthermore, the organ volume measuring apparatus according to an embodiment of the present disclosure may provide an interface for tracking a change of the organ volume of each patient with time.

For example, the volume of the hippocampus may be measured using the organ volume measuring method according to an embodiment of the present disclosure. The amount of reduction in the volume of the hippocampus is related to the occurrence of psychotic symptoms of Alzheimer's disease and dementia, and thus, according to an embodiment, the above-described mental disorder may be diagnosed through measurement of the volume of the hippocampus. In this case, the volume of the hippocampus may be measured based on a medical image, and the medical image may include, for example, CT and MRI images, but the type of the medical image is not limited thereto, and the volume of the hippocampus described above may also be measured using other types of medical images.

As another example, a volume of a liver may be measured using the organ volume measuring method according to an embodiment of the present disclosure. The liver volume is necessary to calculate a ratio of the remaining liver volume with respect to the total liver volume for liver resection of a large amount of liver. In order to predict the donor and recipient's liver function in liver transplant surgery, the donor's liver volume is to be accurately measured before surgery. Therefore, accurate measurement of the volume of the liver according to some embodiments of the present disclosure may bring about a positive effect on a success rate of a liver transplant surgery and the prognosis of the patient. Furthermore, in the case of measuring not only the volume of the liver but also the volume of the spleen in an embodiment, a success rate of the liver surgery and a volume change between the volume of the liver and the volume of the spleen may be accurately measured.

In another example, the volume of a designated cancer tissue may be measured using the organ volume measuring method according to an embodiment of the present disclosure. In this case, a response to an anticancer medicine may be quantified and objectified based on the change in the volume of the specified cancer tissue for a time point before and after treatment using the anticancer medicine.

Hereinafter, a method of determining a progression state of a polycystic kidney or a polycystic liver, which is an example of an apparatus for performing an organ volume measuring method, and an electronic medical device for performing the method, will be described in detail with reference to FIGS. 13 through 15.

In an embodiment, the electronic medical device may include an input module, a memory, and a processor. According to various embodiments, a structure of the electronic medical device may not be limited to those described above. For example, in the electronic medical device, some of the above-described components may be omitted or components not described above may be further included. For example, the electronic medical device may further include an output module that is electrically connected at least to a processor.

The input module may acquire at least one test image. The test image may include a tomographic picture including at least a part of the human body, for example, a kidney or a liver. The test image may be an image in which the kidney or liver region is not specified. For example, the test image may be a tomography image including a kidney or liver of a patient, for whom it is required to measure the volume of the kidney or liver.

According to various embodiments of the present disclosure, there may be a plurality of test images, and the plurality of test images may be a plurality of tomography images taken at a specified interval with respect to at least one target. For example, a first test image may be an image obtained by taking a tomogram of a first cross-section of at least one object, and a second test image may be an image obtained by taking a tomogram of a second cross-section of the at least one object, wherein the second cross-section may be parallel to the first cross-section with a specified interval from the first cross-section. According to various embodiments, the input module may sequentially or simultaneously acquire at least one test image. For example, the input module may acquire the first test image and the second test image sequentially or simultaneously.

According to an embodiment, the input module may acquire a plurality of training images and information on a region of the plurality of training images, the region corresponding to a kidney or a liver, from among the plurality of training images. The plurality of training images may be, for example, a plurality of pieces of sample data for acquiring at least one deep learning model. In an embodiment, the plurality of training images may be images in which designation of a kidney or liver region is completed. For example, a training image may be an image in which designation of a kidney or liver region or measurement of volumes of the kidney or the liver is completed among images acquired by taking a tomogram of a cross-section including the kidney or liver of at least one patient.

According to an embodiment, a training image may be an image in which designation of regions of a plurality of objects is completed. For example, a training image may be an image in which designation of both a region for a liver and a region for a kidney is completed. According to various embodiments of the present disclosure, accuracy of a deep learning model acquired using a training image acquired by performing designation of regions of a plurality of objects may be further improved. For example, when a deep learning model is acquired using training images in which all regions of a plurality of objects are designated, for example, when regions of a liver and a kidney are all designated, the accuracy of designation of regions with respect to the liver and the kidney in a test image may be further improved.

According to an embodiment, designation of regions with respect to the plurality of objects may be performed through single signal processing. For example, in a training image, designation of the liver region and designation of the kidney region may be labeled with a single, same color. According to another embodiment, designation of regions with respect to the plurality of objects may be performed through different signal processings from one another. For example, in a training image, designation of the liver region and designation of the kidney region may be labeled in different colors from each other. When designation of regions with respect to a plurality of objects is done using different signals, a deep learning model having higher accuracy may be expected than a case in which designation of regions is done with a single signal. According to various embodiments, different signal processings on the plurality of objects may be performed using two or more different signals.

According to various embodiments, the input module may sequentially or simultaneously acquire a plurality of training images or information on a specific region from among the plurality of training images. For example, the input module may acquire a plurality of training images of a first group or information on a specific region among the plurality of training images of the first group, and then may further acquire a plurality of training images of a second group or information on a specific region among the plurality of training images of the first group. As another example, the input module may simultaneously a plurality of training images of a first group and a plurality of training images of a second group and information on a specific region among the plurality of training images of the first group and the second group.

According to various embodiments, the input module may include at least one of a camera module, a scan module, a communication module, and a user input module. For example, the input module may include a camera module, and the camera module may capture a test image. In an embodiment, the captured test image may be transmitted to a processor or a memory. As another example, the input module may include a scan module, and the scan module may scan an already captured test image and convert the same into an electrical signal. In an embodiment, the converted electrical signal may be transmitted to a processor or a memory. As another example, the input module may include a communication module, and the communication module may acquire a test image from an external electronic device through wireless communication or wired communication. In an embodiment, the acquired test image may be transmitted to a processor or a memory.

According to an embodiment, the input module may acquire a user input as well as a test image. For example, the input module may include a user input module, and the user input module may acquire, from a user, various inputs for processing a test image. For example, the input module may acquire, from a user, distances between cross-sections respectively corresponding to a plurality of test images.

The memory may include a volatile memory or a nonvolatile memory. The volatile memory may include, for example, random access memory (RAM) (e.g., DRAM, SRAM, or SDRAM). The nonvolatile memory may include, for example, OTPROM (one time programmable read-only memory; ROM), PROM (programmable read-only memory), EPROM (erasable programmable read-only memory), EEPROM (electrically erasable programmable read-only memory), mask ROM, flash ROM, flash memory, a hard drive, or a solid state drive (SSD).

According to various embodiments, the memory may store, for example, at least one other software component of an electronic medical device, for example, an instruction, information, or data related to a program. In various embodiments, the memory may store information acquired from an input module or information processed by a processor. In various embodiments, the information acquired from the input module may include, for example, a test image, a training image, information on a specific region of the training image, for example, a region corresponding to a kidney or liver, or a user input. In various embodiments, information processed by the processor may include a deep learning model obtained from, for example, information on a specific region of a test image, for example, a region corresponding to the kidney or liver, a training image, and information on a specific region of the training image.

The processor may include one or more of a central processing unit (CPU), an application processor (AP), or a communication processor (CP). In various embodiments, the processor may control at least one other component (e.g., hardware or software component) of an electronic medical device connected to the processor and perform various data processing and operations by driving, for example, an operating system or an application program. For example, the processor may perform an operation on an instruction or data received from at least one of other components (e.g., an input module) and store a result thereof in a memory.

According to an embodiment, the processor may acquire at least one deep learning model based on a plurality of training images and information on a specific region from among the plurality or training images, for example, a region corresponding to the kidney or the liver, stored in the memory. In an embodiment, the processor may update the deep learning model. For example, the processor may acquire a new training image and information on a region corresponding to the kidney or liver among the new training image and update the deep learning model stored in the memory based on the acquired image and the acquired information.

According to an embodiment, the processor may acquire at least one test image through an input module, and detect a region corresponding to a kidney or a region corresponding to a liver from among the at least one test image based on a deep learning model stored in a memory.

According to an embodiment, the processor may estimate a volume of a kidney or a liver included in at least one test image. For example, the processor may acquire an area of a detected region of at least one test image, and estimate a volume of the kidney or the liver based on the acquired area. For example, the processor may receive, from a user via an input module, an interval at which at least one test image is captured, for example, an interval between a cross-section from which a first test image is captured and a cross-section from which a second test image is captured, and the acquired area, and estimate a volume of the kidney or the liver based on the interval and the acquired area. According to an embodiment, the processor may determine a progression state of a polycystic kidney or a polycystic liver with respect to a kidney or liver corresponding to at least one test image based on the estimated volume of the kidney or liver.

According to various embodiments, the electronic medical device may further include an output module. The output module may include, for example, at least one display. The output module may be electrically connected to the processor and may output data transmitted from the processor in a form that is recognizable by a user. In various embodiments, the form recognizable by a user may include at least one of a text, voice, an image, or a video. According to various embodiments of the present disclosure, the processor may display a region corresponding to the kidney or liver, or the volume of the kidney or liver, among the test images by using the output module. According to another embodiment, the processor may display a progression state of the polycystic kidney or the polycystic liver with respect to the kidney or the liver by using the output module.

Figure 13:
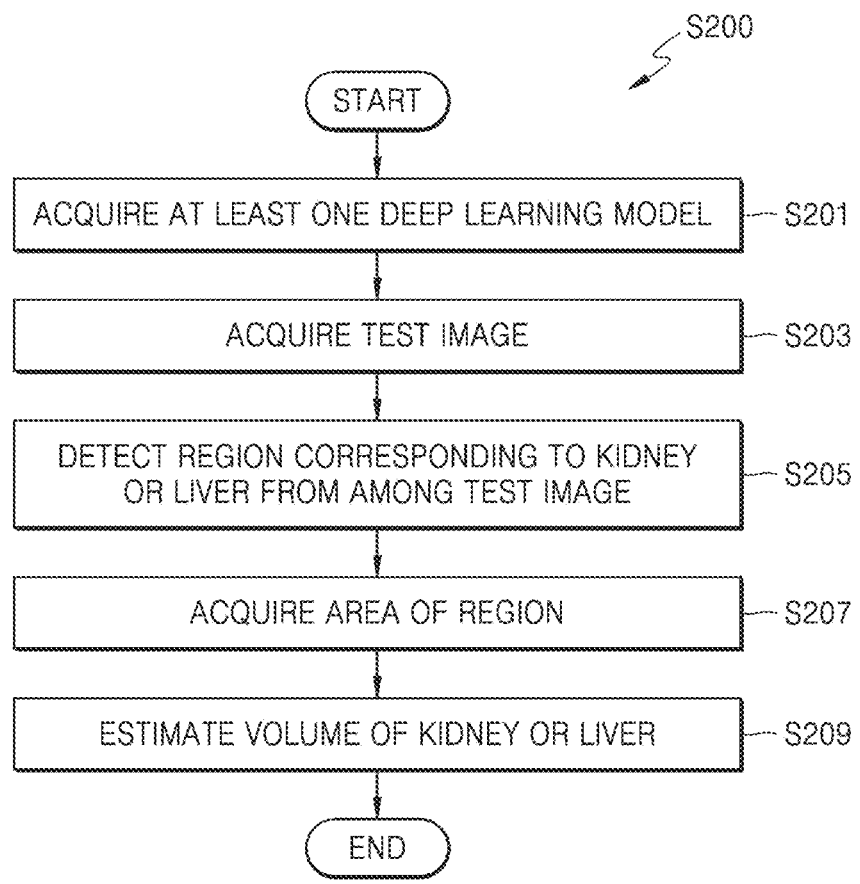
FIG. 13 is a flowchart of a method, performed by an electronic medical device, of estimating a volume of a kidney or a liver, according to an embodiment of the present disclosure.

FIG. 13 is a flowchart of a method, by an electronic medical device according to an embodiment, of estimating a volume of a kidney or liver.

Referring to FIG. 13, a method S200 of estimating a volume of a kidney or liver, performed by the electronic medical device, may include operations S201 through S209. According to various embodiments, in the method S200, at least one of operations S201 through S209 may be omitted or operations not illustrated in FIG. 13 may be further included. According to an embodiment, operations S201 through S209 may be understood as a method executed by the above-described electronic medical device or processor.

In operation S201, the electronic medical device may acquire at least one deep learning model. In an embodiment, the at least one deep learning model may be acquired based on a plurality of training images acquired through an input module and information on a kidney region or a liver region among the plurality of training images.

According to an embodiment, the at least one deep learning model may be a model for extracting a kidney or liver region from an image including a kidney or liver. For example, the at least one deep learning model may be a model for inducing a relationship between an image and a region, for example, weights with respect to a plurality of elements included in an image. In various embodiments, a plurality of factors and weights may be different based on a training method or data of a deep learning model. According to an embodiment, the training method may include v-net training.

In an embodiment, a plurality of training images and information on a kidney or liver region among the plurality of training images may be a set of previously acquired data. For example, a plurality of training images may be acquired from data previously accumulated in a medical institution or the like. In an embodiment, information on a region corresponding to the kidney or liver among the plurality of training images may be acquired through preprocessing of the plurality of training images. The preprocessing may include, for example, performing an operation of directly displaying a region on the plurality of training images in an existing medical institution or the like with respect to the plurality of training images. The accuracy of the at least one deep learning model may be improved as the number and types of the plurality of training images increase.

In various embodiments, operation S201 may be omitted. For example, when there is at least one deep learning model already stored in a memory, the electronic medical device may skip operation S201 and perform operation S203. In this case, the electronic medical device may use the at least one deep learning model already stored in the memory in operations S203 through S209 below.

In operation S203, the electronic medical device may acquire a test image. The test image may be acquired through at least one of an input module, for example, a camera module, a scan module, and a communication module. In an embodiment, the test image may be a two-dimensional tomography image of a patient's body requiring measurement of a kidney or liver volume.

In operation S205, the electronic medical device may detect a region corresponding to the kidney or liver from among the test image acquired in operation S203. For example, the electronic medical device may apply the deep learning model acquired in operation 201 to the acquired test image. In an embodiment, the deep learning model may include weight information with respect to a plurality of elements, and the weights may be applied to a plurality of elements included in the test image. Accordingly, the electronic medical device may detect, from the test image, a specific region corresponding to the deep learning model, for example, a region corresponding to the kidney or liver.

In operation S207, the electronic medical device may acquire an area of the region detected in operation S205. For example, the electronic medical device may acquire the area based on a size of a test image, a magnification of the test image, and/or a ratio of the detected region in the test image.

In operation S209, the electronic medical device may estimate a volume of the kidney or liver included in the test image acquired in operation S203. For example, when a test image of an object, for example, a human body including a kidney or liver is continuously captured at specified intervals, the electronic medical device may estimate the volume of the kidney or liver based on the specified intervals. For example, the test image may include a plurality of images successively captured with respect to an object at specified intervals. The electronic medical device may continuously perform operation S207 on each of the plurality of images, and may estimate the volume of the kidney or liver based on results of operation S207 and the specified intervals.

According to various embodiments, the electronic medical device may further include an output module, and may display the volume of the kidney or liver estimated in operation S209 on the output module. Accordingly, the user may check the progression of the polycystic kidney or the polycystic liver with respect to a patient corresponding to the test image.

Through operations S201 to S209, the electronic medical device may accurately and quickly estimate the volume of the kidney or the liver included in the test image.

Figure 14:
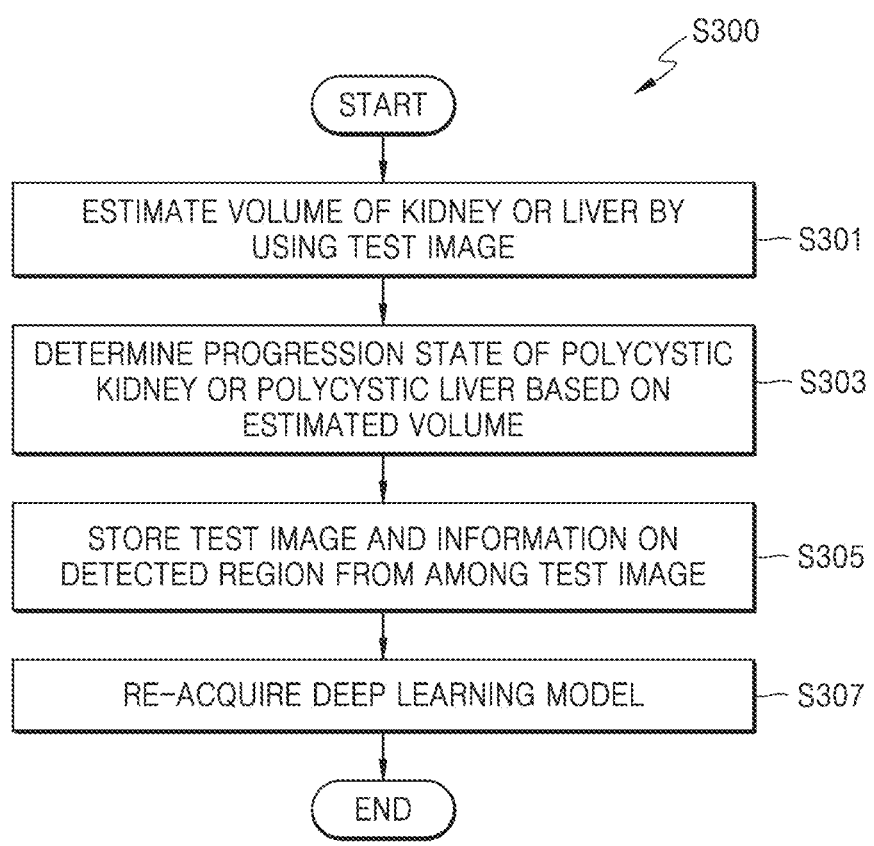
FIG. 14 is a flowchart of a method, performed by an electronic medical device, of estimating a volume of a kidney or a liver and updating a deep learning model, performed by an electronic medical device, according to an embodiment of the present disclosure.

FIG. 14 is a flowchart of a method, performed by an electronic medical device, of estimating a volume of kidney or liver and updating a deep learning model, according to an embodiment.

Referring to FIG. 14, a method S300, performed by an electronic medical device, of estimating a volume of a kidney or liver and updating a deep learning model may include operations S301 through S307. According to various embodiments, in the method S300, at least one of operations S301 through S307 may be omitted or operations not illustrated in FIG. 14 may be further included. According to an embodiment, operations S301 through S307 may be understood as a method executed by the above-described electronic medical device or processor. In the description of FIG. 14, description of details already provided above with reference to FIG. 13 may be omitted.

In operation S301, the electronic medical device may estimate a volume of a kidney or liver included in a test image by using the test image. For example, the electronic medical device may estimate the volume of the kidney or liver included in the test image by performing operations S201 through S209 shown in FIG. 13.

In operation S303, the electronic medical device may determine a progression state of a polycystic kidney or a polycystic liver, based on the volume of the kidney or liver estimated in operation S301. For example, the electronic medical device may acquire information on a reference volume of a patient's kidney or liver corresponding to the test image through an input module. According to various embodiments, the reference volume may be a volume of a normal kidney or liver with respect to the patient, or a volume of a kidney or liver, the volume being measured several months before with respect to the patient.

According to an embodiment, the electronic medical device may calculate a level of the volume of the kidney or liver acquired in operation S301 compared to the reference volume, for example, how many times the volume of the kidney or liver acquired in operation S301 is compared to the reference volume. The electronic medical device may determine a progression state of the polycystic kidney or polycystic liver of the patient based on a result of the calculating.

In operation S305, the electronic medical device may store the test image and information on the detected region from among the test image in a memory. When a region corresponding to the kidney or liver is detected from the test image through operation S301, the test image and the detected region may be used as a new training image and information on a specific region among the new training image. As the accuracy of the deep learning model may increase as the number of training images increases, the electronic medical device may store the new training image and the information on the specific region of the new training image in the memory.

In operation S307, the electronic medical device may update (or re-acquire) the deep learning model. As the electronic medical device acquires the new training image and the information on the specific region of the new training image through operation S305, the electronic medical device may re-acquire a new deep learning model together with a plurality of training images and information on a specific region among the plurality of training images, which are previously stored in the memory, or update an existing deep learning model. Accordingly, the electronic medical device may develop the deep learning model and more accurately detect a region corresponding to the kidney or liver among the test image.

Through operations S301 to S307, the electronic medical device may accurately and quickly determine a progression state of the polycystic kidney or the polycystic liver, and improve the accuracy of the deep learning model.

Figure 15:
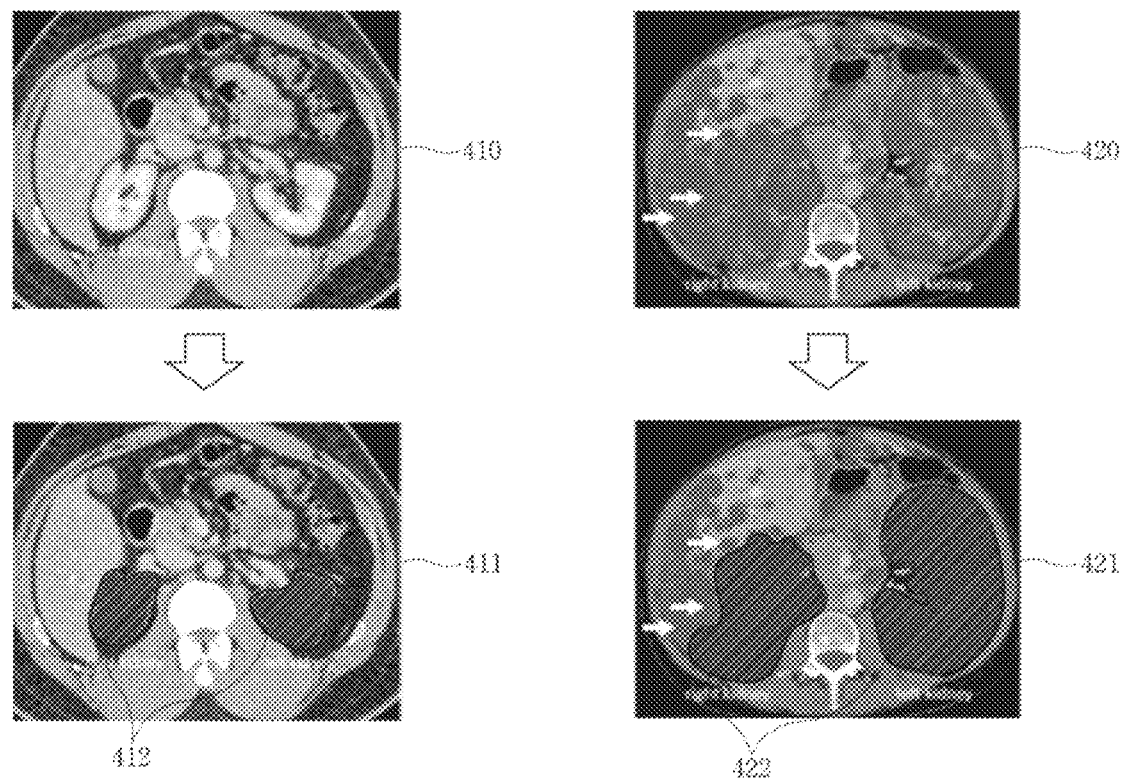
FIG. 15 illustrates a result of extracting and displaying, by an electronic medical device, a kidney or liver region from among at least one test image, according to an embodiment of the present disclosure.

FIG. 15 illustrates a result of extracting and displaying a kidney or liver region from among at least one test image by an electronic medical device, according to an embodiment.

Referring to FIG. 15, a first test image 410 and a second test image 420 are illustrated. The first test image 410 and the second test image 420 may be images acquired by taking a tomography image of a cross-section of a part of the body, for example, a part including a kidney. Referring to the first test image 410 and the second test image 420, it may be difficult to clearly determine the boundary between the kidney and other parts with the naked eye.

In an embodiment, when the deep learning model according to the present disclosure is applied to each of the first test image 410 and the second test image 420, a first processed image 411 and a second processed image 421 may be acquired. The first processed image 411 and the second processed image 421 may be respectively images in which a first region 412 and a second region 422 corresponding to the kidney are displayed in the first test image 410 and the second test image 420.

According to an embodiment, a test image, for example, the first test image 410 or the second test image 420 may include at least one piece of identification information. For example, the identification information may include at least one of personal information about a patient, a photographing date, a photographing time, a photographing location, distances between cross-sections, or scale information. According to an embodiment, before applying the deep learning model according to the present disclosure, a preprocessing process, for example, a process of deleting the identification information from the test image (410 or 420) or a process of extracting, from the test image (410 or 420), other regions except for the identification information may be performed. The preprocessing process may be performed, for example, by the above-described processor.

In an embodiment, when a preprocessing process is performed on the test image (410 or 420), the test image (410 or 420) may be de-identified, and extraction accuracy with respect to a target region may be improved. That is, the preprocessing process may improve the accuracy of region extraction of the deep learning model.

According to an embodiment, the first region 412 and the second region 422 may be separated from the first processed image 411 and the second processed image 421 to be extracted. The electronic medical device may acquire areas of the extracted first region 412 and the second region 422, and may estimate a volume of the kidney included in the first test image 410 and the second test image 420, accordingly.

The apparatus described above may be embodied by a hardware component, a software component, and/or a combination of a hardware component and a software component. For example, the apparatuses and components described in the embodiments may be realized using at least one or more general-use computers or special-purpose computers, such as a processor, a controller, an ALU (arithmetic logic unit0, a digital signal processor, a microcomputer, an FPA (field-programmable array), a PLU (programmable logic unit), a microprocessor, or any type of apparatus that may execute and respond to an instruction. A processing device may execute an operating system (OS) and one or more software applications running on the OS. Further, the processing device may access, store, manipulate, process, and generate data in response to the execution of software. For ease of understanding, it may be described that a single processing apparatus is used, but one of ordinary skill in the art will be aware that the processing apparatus may include a plurality of processing elements and/or a plurality of types of processing elements. For example, the processing apparatus may include a plurality of processors or a single processor, and a controller. In addition, the processing device may have another processing configuration, such as a parallel processor.

The software may include a computer program, code, instructions, or a combination of one or more of the foregoing, and may configure the processing apparatus so that the processing apparatus can operate as intended, or to independently or collectively give instructions to the processing apparatus. The software and/or the data may be permanently or temporarily embodied in any type of machine, component, physical device, virtual equipment, computer storage media or devices, or transmitted signal waves, such that the software and/or the data is interpreted by the processing apparatus or provides an instruction or data to the processing device. The software may be distributed over a networked computer system and stored or executed in a distributed manner. The software and the data may be stored on one or more computer-readable recording media.

The method according to the embodiments may be embodied as program instructions executable by various computer means and may be recorded on a computer-readable recording medium. The computer-readable recording medium may include program instructions, data files, data structures, and the like separately or in combinations. The program instructions to be recorded on the computer-readable recording medium may be specially designed and configured for the embodiments or may be well-known to and available to one of ordinary skill in the art of computer software. Examples of the computer-readable recording medium include magnetic media (e.g., hard disks, floppy disks, magnetic tapes, etc.), optical media (e.g., CD-ROMs, or DVDs), magneto-optical media (e.g., floptical disks), and hardware devices specifically configured to store and execute program instructions (e.g., ROM, RAM, flash memories, etc.). Examples of the program instructions are advanced language codes that can be executed by a computer by using an interpreter or the like as well as machine language codes made by a compiler. The hardware devices can be configured to function as one or more software modules so as to perform operations according to the embodiments, or vice versa.

While the present disclosure has been particularly shown and described with reference to embodiments thereof, it will be understood by those of ordinary skill in the art that various changes in form and details may be made therein. For example, an appropriate result may be attained even when the above-described techniques are performed in a different order from the above-described method, and/or components, such as the above-described system, structure, device, and circuit, are coupled or combined in a different form from the above-described methods or substituted for or replaced by other components or equivalents thereof.

Thus, other implementations, other embodiments, and those equivalent to the claims also fall within the scope of the claims to be described later.

The invention claimed is:

1. A method, performed by a computing device, of measuring a volume of an organ, the method comprising:

acquiring a plurality of captured images of the organ and photographing metadata and preprocessing the plurality of images to acquire a plurality of image patches of a specified size;

inputting the plurality of image patches into a three-dimensional (3D) convolutional neural network (CNN)-based neural network model and estimating an organ region corresponding to each of the plurality of image patches;

measuring a volume of the organ by using an area of the estimated organ region and the photographing metadata;

measuring an uncertainty value of the 3D CNN-based neural network model and uncertainty values of the plurality of images based on a result of estimating by the 3D CNN-based neural network model;

modifying at least one of the plurality of images based on the uncertainty values of the plurality of images;

wherein the modifying of at least one of the plurality of images comprises:

detecting one or more images in which the uncertainty values of the plurality of images are equal to or greater than a reference value; and modifying the detected image based on a user input with respect to the organ region of the detected image; and modifying a labeling policy of the 3D CNN-based neural network model based on the uncertainty value of the 3D CNN-based neural network model; and training the neural network model by setting weights of the plurality of images according to the modified labeling policy and assigning, to the modified image, a greater weight than that assigned to a non-modified image.

2. The method of claim 1, wherein the plurality of captured images of the organ comprise a CT image acquired from a digital imaging and communications in medicine (DICOM) file and a labeling image with respect to the organ, and the photographing metadata comprises pixel spacing data and image depth data with respect to each of the plurality of images.

3. The method of claim 1, wherein the acquiring of the plurality of image patches comprises performing data augmentation on a first image included in the plurality of images to generate a plurality of images from the first image and acquiring a plurality of image patches by preprocessing the generated plurality of images, and wherein the data augmentation comprises one or more of spatial augmentation, color augmentation, noise augmentation, or cropping of the image.

4. The method of claim 1, wherein the plurality of images comprise a plurality of 3D images acquired by capturing images of the organ, and the acquiring of the plurality of image patches comprises sliding in a depth direction with respect to the plurality of 3D images and acquiring the plurality of image patches of a specified size.

5. The method of claim 1, wherein the 3D CNN-based neural network model performs dropout in a learning operation and an inference operation, and the uncertainty value of the 3D CNN-based neural network model is measured based on a variance value with respect to a probability distribution of resultant data in the inference operation of the 3D CNN-based neural network model.

6. The method of claim 5, wherein the uncertainty values of the plurality of images are measured based on an estimated variance value of the resultant data in the inference operation of the 3D CNN-based neural network model.

7. An organ volume measuring apparatus comprising:
a memory storing instructions; and
one or more processors configured to execute the instructions to perform the method of claim 1.

8. The organ volume measuring apparatus of claim 7, wherein the plurality of captured images of the organ comprise a CT image acquired from a digital imaging and communications in medicine (DICOM) file and a labeling image with respect to the organ, and the photographing metadata comprises pixel spacing data and image depth data with respect to each of the plurality of images.

9. The organ volume measuring apparatus of claim 7, wherein the processor is further configured to perform data augmentation on a first image included in the plurality of images to generate a plurality of images from the first image and acquire a plurality of image patches by preprocessing the generated plurality of images, and wherein the data augmentation comprises one or more of spatial augmentation, color augmentation, noise augmentation, or cropping of the image.

10. The organ volume measuring apparatus of claim 7, wherein the plurality of images comprise a plurality of 3D images acquired by capturing images of the organ, and wherein the processor is further configured to slide in a depth direction with respect to the plurality of 3D images and acquire the plurality of image patches of a specified size.

11. The organ volume measuring apparatus of claim 7, wherein the 3D CNN-based neural network model performs dropout in a learning operation and an inference operation, and the uncertainty value of the 3D CNN-based neural network model is configured to be measured based on a variance value with respect to a probability distribution of resultant data in the inference operation of the 3D CNN-based neural network model.

12. The organ volume measuring apparatus of claim 11, wherein the uncertainty values of the plurality of images are configured to be measured based on an estimated variance value of the resultant data in the inference operation of the 3D CNN-based neural network model.

* * * * *